United States Patent
Robert et al.

(10) Patent No.: US 9,212,234 B2
(45) Date of Patent: *Dec. 15, 2015

(54) PROCESS FOR PRODUCING HIGH MOLECULAR WEIGHT POLYETHYLENE

(75) Inventors: Dominique Robert, Dinslaken (DE); Julia Hufen, Rheinberg (DE); Kerstin Lüdtke, Markkleeberg (DE); Bjorn Rinker, Hunxe (DE); Jens Ehlers, Hamminkeln (DE)

(73) Assignee: TICONA GMBH, Sulzbach (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/700,879

(22) PCT Filed: Jul. 1, 2011

(86) PCT No.: PCT/IB2011/002283
§ 371 (c)(1),
(2), (4) Date: Nov. 29, 2012

(87) PCT Pub. No.: WO2012/004680
PCT Pub. Date: Jan. 12, 2012

(65) Prior Publication Data
US 2013/0072649 A1 Mar. 21, 2013

Related U.S. Application Data

(60) Provisional application No. 61/361,703, filed on Jul. 6, 2010.

(51) Int. Cl.
C08F 4/76 (2006.01)
C08F 110/02 (2006.01)
C07C 43/23 (2006.01)
C07F 7/00 (2006.01)
C08F 4/60 (2006.01)

(52) U.S. Cl.
CPC . *C08F 4/76* (2013.01); *C07C 43/23* (2013.01); *C07F 7/00* (2013.01); *C07F 7/006* (2013.01); *C08F 110/02* (2013.01); *C08F 4/60193* (2013.01)

(58) Field of Classification Search
CPC .................................................. C08F 4/60193
USPC ................. 526/172, 129, 130, 160, 161, 352
See application file for complete search history.

(56) References Cited

U.S. PATENT DOCUMENTS

| 4,760,120 A | 7/1988 | Sano et al. |
| 5,444,145 A | 8/1995 | Brant et al. |
| 5,741,451 A | 4/1998 | Dunbar et al. |
| 5,780,562 A | 7/1998 | Shimizu et al. |
| 6,017,975 A | 1/2000 | Saum et al. |
| 6,051,525 A | 4/2000 | Lo et al. |
| 6,211,311 B1 | 4/2001 | Wang et al. |
| 6,265,504 B1 * | 7/2001 | Liu et al. ........................ 526/161 |
| 6,486,089 B1 | 11/2002 | Kissin et al. |
| 6,503,439 B1 | 1/2003 | Burstein |
| 6,559,249 B2 | 5/2003 | Yang et al. |
| 6,767,975 B1 | 7/2004 | Liu |
| 6,852,811 B1 | 2/2005 | Carnahan et al. |
| 7,060,848 B2 * | 6/2006 | Boussie et al. ................... 556/54 |
| 7,091,292 B2 * | 8/2006 | Boussie et al. ................ 526/172 |
| 7,157,532 B2 | 1/2007 | Payer et al. |
| 7,205,363 B2 | 4/2007 | Dickey et al. |
| 7,259,125 B2 * | 8/2007 | Apecetche et al. ........... 502/232 |
| 7,598,329 B2 | 10/2009 | Panitzky et al. |
| 8,637,618 B2 * | 1/2014 | Diamond et al. ............. 526/161 |
| 2004/0110853 A1 | 6/2004 | Wang et al. |
| 2004/0161605 A1 | 8/2004 | Simmelink et al. |
| 2007/0225390 A1 | 9/2007 | Wang et al. |
| 2008/0051537 A1 | 2/2008 | Carnahan et al. |
| 2009/0163679 A1 | 6/2009 | Do Nascimento et al. |
| 2009/0163682 A1 | 6/2009 | Miranda et al. |
| 2009/0171043 A1 | 7/2009 | Miranda |

FOREIGN PATENT DOCUMENTS

| CN | 101654492 A | 2/2010 |
| DE | 3833445 A1 | 4/1990 |
| EP | 186995 A2 | 7/1986 |
| EP | 575840 B1 | 6/1993 |
| EP | 0622379 B1 | 4/1994 |
| EP | 0643078 | 8/1994 |
| EP | 0676418 B1 | 3/1995 |
| EP | 0798306 A1 | 3/1997 |
| WO | 91/02012 | 2/1991 |
| WO | 9719959 | 6/1997 |
| WO | 98/41576 A1 | 9/1998 |
| WO | 01/21668 A1 | 3/2001 |
| WO | 0155231 A1 | 8/2001 |

(Continued)

OTHER PUBLICATIONS

International Search Report issued in related PCT/IB2011/002250 mailed Feb. 13, 2012.

Makio, et al., "FI Catalysts: A New Family of High Performance Catalysts for Olefin Polymerization", Adv. Synth. Catal 2002, 344,477-493.

Tisse et al. "Influence of Silica Support Size on the Polymerization of Ethylene Using a Supported Metallocene Catalyst", Macromol. Symp., 2009, 285, pp. 45-51.

Hlatky, "Heterogeneous Single-Site Catalysts for Olefin Polymerization," Chem. Rev. 2000, 100, 1347-1376.

(Continued)

*Primary Examiner* — Rip A Lee
(74) *Attorney, Agent, or Firm* — Roberts Mlotkowski Safran & Cole, P.C.

(57) ABSTRACT

In a process for producing high molecular weight polyethylene, ethylene is contacted with a slurry of a catalyst composition comprising a Group 4 metal complex of a phenolate ether ligand under polymerization conditions comprising a temperature of about 20° C. to less than 90° C. and a pressure of about 4 bar to about 40 bar.

21 Claims, No Drawings

(56) References Cited

FOREIGN PATENT DOCUMENTS

| WO | 02/094891 A2 | 11/2002 |
| WO | 03091262 A1 | 11/2003 |
| WO | 2005108406 A1 | 11/2005 |
| WO | 2006020624 A1 | 2/2006 |
| WO | 2007051612 A1 | 5/2007 |
| WO | 2010078164 A1 | 7/2010 |
| WO | 2011087520 A1 | 7/2011 |
| WO | 2011140053 A1 | 11/2011 |
| WO | 2012004674 A2 | 1/2012 |
| WO | 2012004675 A2 | 1/2012 |
| WO | 2012004676 A2 | 1/2012 |
| WO | 2012004680 A2 | 1/2012 |
| WO | 2012004681 A2 | 1/2012 |
| WO | 2012004683 A2 | 1/2012 |
| WO | 2012006230 A1 | 1/2012 |

OTHER PUBLICATIONS

International Search Report issued in related PCT/IB2011/002274 mailed Feb. 6, 2012.
International Search Report issued in related PCT/US2011/042759 mailed Sep. 14, 2011.
International Search Report issued in related PCT/IB2011/002322 mailed Feb. 6, 2012.
International Search Report issued in related PCT/IB2011/002283 mailed Feb. 6, 2012.
International Search Report issued in related PCT/IB2011/002218 mailed Jan. 17, 2012.
International Search Report issued in related PCT/IB2011/002284 mailed Feb. 6, 2012.
Kiesewetter, et al., "Stereospecific Octahedral Group 4 Bis(phenolate) Ether Complexes for Olefin Polymerization", J. Am. Chem. Soc. 2010, 132, pp. 5566-5567.

* cited by examiner

PROCESS FOR PRODUCING HIGH MOLECULAR WEIGHT POLYETHYLENE

CROSS-REFERENCE TO RELATED APPLICATIONS

The present Application is a U.S. National Phase of PCT/IB2011/002283 filed on Jul. 1, 2011, which claims priority to U.S. provisional Application 61/361,703 filed on Jul. 6, 2010. The PCT and Provisional Applications are hereby incorporated by reference in their entirety into the present application.

FIELD

The present invention relates to process for producing high molecular weight polyethylene.

BACKGROUND

The term "high molecular weight polyethylene" is generally used to define polyethylene having a molecular weight of at least $3\times10^5$ g/mol as determined by ASTM 4020 and, as used herein is intended to include very-high molecular weight polyethylene or VHMWPE (generally characterized as polyethylene having a molecular weight of at least $1\times10^6$ g/mol and less $3\times10^6$ g/mol as determined by ASTM 4020) and ultra-high molecular weight polyethylene or UHMWPE (generally characterized as polyethylene having a molecular weight of at least $3\times10^6$ g/mol as determined by ASTM 4020).

High molecular weight polyethylenes are valuable engineering plastics, with a unique combination of abrasion resistance, surface lubricity, chemical resistance and impact strength. Thus, in solid, compression molded form, these materials find application in, for example, machine parts, linings, fenders, and orthopedic implants. In sintered porous form, they find application in, for example, filters, aerators and pen nibs.

Currently, high molecular weight polyethylenes are generally produced using Ziegler-Natta catalysts, see, for example, EP186995, DE3833445, EP575840 and U.S. Pat. No. 6,559,249. However, these catalysts have certain limitations with regard to the molecular weight and molecular weight distribution of the polymers that can be produced. There is therefore significant interest in developing alternative catalyst systems for producing high molecular weight polyethylene.

Other known catalysts for olefin polymerization are single site catalysts. According to the present state of technology, high molecular weight polyethylenes are manufactured using these catalysts only in exceptional cases and under economically unprofitable conditions. Thus, with heterogeneous constrained-geometry catalysts, high molecular weight polyethylene is produced only with moderate activity and increased long chain branching, which can lead to reduced hardness and abrasion properties. With so-called phenoxy-imine catalysts, high molecular weight polyethylene is obtained only at low activity at economically disadvantageous temperature levels. Examples of these and other metallocene catalysts are described in WO9719959, WO0155231, Adv. Synth. Catal 2002, 344, 477-493, EP0798306 and EP0643078.

One other potentially useful catalyst system for producing UHMWPE comprises a Group 4 metal complex of a bis (phenolate) ether ligand such as disclosed in International Publications Nos. WO 2003/091262 and WO 2005/108406, the entire disclosures of which are incorporated herein by reference. Research has, however, shown that, although this system provides an effective catalyst for the slurry phase polymerization of UHMWPE with molecular weights unachievable with Ziegler-Natta catalysts, achieving satisfactory catalyst activity is surprisingly dependent on maintaining the process pressure and temperature within narrowly defined limits.

United States Patent Application Publication No. 2008/0051537 discloses a supported, heterogeneous catalyst composition comprising: 1) a substrate comprising a solid, particulate, high surface area, surface modified, inorganic oxide compound, 2) a Group 4 metal complex of a bis(phenolate) ether ligand; and optionally 3) an activating cocatalyst for the metal complex. The catalyst composition is said to be useful for the polymerization of propylene, 2-methyl-4-butene, and mixtures of ethylene with one or more C3-8 α-olefins, especially propylene, 1-butene, 1-hexene, 2-methyl-4-butene, or 1-octene.

SUMMARY

In one aspect, the present invention resides in a process for producing high molecular weight polyethylene, the process comprising: contacting ethylene under polymerization conditions with a slurry of a catalyst composition comprising a Group 4 metal complex of a phenolate ether ligand, wherein the polymerization conditions comprise a temperature of about 20° C. to less than 90° C. and a pressure of about 4 bar to about 40 bar.

Conveniently, the polymerization conditions comprise a temperature of about 50° C. to about 85° C. and a pressure of about 4 bar to about 20 bar.

Conveniently, the Group 4 metal complex is deposited on a particulate support. Generally, the particulate support has an average particle size, d50, of less than 58 microns, such as less than 50 microns, for example from about 4 to about 20 microns. In one embodiment, the particulate support comprises an inorganic oxide, such as silica.

Conveniently, the Group 4 metal complex is a complex of a bis(phenolate) ether ligand, such as a ligand obeying the formula:

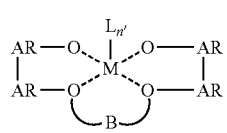

(V)

wherein at least two of the bonds from the oxygens (O) to M are covalent, with the other bonds being dative; AR is an aromatic group that can be the same or different from the other AR groups with each AR being independently selected from the group consisting of optionally substituted aryl and optionally substituted heteroaryl; B is a bridging group having from 3 to 50 atoms not counting hydrogen atoms and is selected from the group consisting of optionally substituted divalent hydrocarbyl and optionally substituted divalent heteroatom-containing hydrocarbyl; M is a metal selected from the group consisting of Hf and Zr; each L is independently a moiety that forms a covalent, dative or ionic bond with M; and n' is 1, 2, 3 or 4.

In one embodiment, the bis(phenolate) ether ligand obeys the formula:

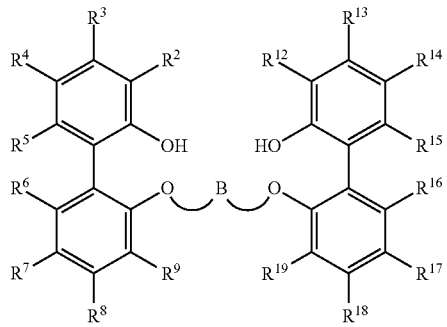

wherein each of $R^2, R^3, R^4, R^5, R^6, R^7, R^8, R^9, R^{12}, R^{13}, R^{14}, R^{15}, R^{16}, R^{17}, R^{18},$ and $R^{19}$ is independently selected from the group consisting of hydrogen, halogen, and optionally substituted hydrocarbyl, heteroatom-containing hydrocarbyl, alkoxy, aryloxy, silyl, boryl, phosphino, amino, alkylthio, arylthio, nitro, and combinations thereof; optionally two or more R groups can combine together into ring structures (for example, single ring or multiple ring structures), with such ring structures having from 3 to 12 atoms in the ring (not counting hydrogen atoms); and B is a bridging group having from 3 to 50 atoms not counting hydrogen atoms and is selected from the group consisting of optionally substituted divalent hydrocarbyl and optionally substituted divalent heteroatom-containing hydrocarbyl.

In a further aspect, the invention resides in a composition of matter having one of the following formulae:

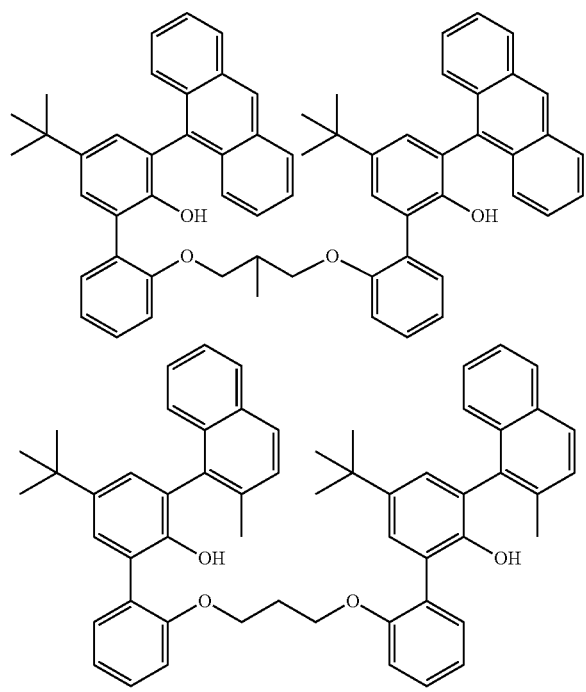

and its use as a ligand in producing a Group 4 metal complex useful in a catalyst composition for polymerizing olefins, particularly ethylene.

DETAILED DESCRIPTION

Described herein is a slurry polymerization process for producing polyethylene having a molecular weight of at least $3 \times 10^5$ g/mol, as determined by ASTM 4020, in the presence of a catalyst composition comprising, as an active component, a Group 4 metal complex of a phenolate ether ligand. In the present process, the temperature and pressure of the process are controlled so as to maximize catalyst activity while also producing a polymerized product in the form of the free flowing powder required for ease of processing.

DEFINITIONS

As used herein, the phrase "characterized by the formula" is not intended to be limiting and is used in the same way that "comprising" is commonly used. The term "independently selected" is used herein to indicate that the groups in question—e.g., $R^1, R^2, R^3, R^4,$ and $R^5$—can be identical or different (e.g., $R^1, R^2, R^3, R^4,$ and $R^5$ may all be substituted alkyls, or $R^1$ and $R^2$ may be a substituted alkyl and $R^3$ may be an aryl, etc.). Use of the singular includes use of the plural and vice versa (e.g., a hexane solvent, includes hexanes). A named R group will generally have the structure that is recognized in the art as corresponding to R groups having that name. The terms "compound" and "complex" are generally used interchangeably in this specification, but those of skill in the art may recognize certain compounds as complexes and vice versa. For the purposes of illustration, representative certain groups are defined herein. These definitions are intended to supplement and illustrate, not preclude, the definitions known to those of skill in the art.

"Optional" or "optionally" means that the subsequently described event or circumstance may or may not occur, and that the description includes instances where said event or circumstance occurs and instances where it does not. For example, the phrase "optionally substituted hydrocarbyl" means that a hydrocarbyl moiety may or may not be substituted and that the description includes both unsubstituted hydrocarbyl and hydrocarbyl where there is substitution.

The term "alkyl" as used herein refers to a branched or unbranched saturated hydrocarbon group typically although not necessarily containing 1 to about 50 carbon atoms, such as methyl, ethyl, n-propyl, isopropyl, n-butyl, isobutyl, sec-butyl, t-butyl, octyl, decyl, and the like, as well as cycloalkyl groups such as cyclopentyl, cyclohexyl and the like. Generally, although again not necessarily, alkyl groups herein may contain 1 to about 20 carbon atoms. "Substituted alkyl" refers to alkyl substituted with one or more substituent groups (e.g., benzyl or chloromethyl), and the terms "heteroatom-containing alkyl" and "heteroalkyl" refer to alkyl in which at least one carbon atom is replaced with a heteroatom (e.g., —$CH_2OCH_3$ is an example of a heteroalkyl).

The term "alkenyl" as used herein refers to a branched or unbranched hydrocarbon group typically although not necessarily containing 2 to about 50 carbon atoms and at least one double bond, such as ethenyl, n-propenyl, isopropenyl, n-butenyl, isobutenyl, octenyl, decenyl, and the like. Generally, although again not necessarily, alkenyl groups herein contain 2 to about 20 carbon atoms. "Substituted alkenyl" refers to alkenyl substituted with one or more substituent groups, and the terms "heteroatom-containing alkenyl" and "heteroalkenyl" refer to alkenyl in which at least one carbon atom is replaced with a heteroatom.

The term "alkynyl" as used herein refers to a branched or unbranched hydrocarbon group typically although not necessarily containing 2 to about 50 carbon atoms and at least one triple bond, such as ethynyl, n-propynyl, isopropynyl, n-butynyl, isobutynyl, octynyl, decynyl, and the like. Generally, although again not necessarily, alkynyl groups herein may have 2 to about 20 carbon atoms. "Substituted alkynyl" refers to alkynyl substituted with one or more substituent groups, and the terms "heteroatom-containing alkynyl" and "heteroalkynyl" refer to alkynyl in which at least one carbon atom is replaced with a heteroatom.

The term "aromatic" is used in its usual sense, including unsaturation that is essentially delocalized across several bonds around a ring. The term "aryl" as used herein refers to a group containing an aromatic ring. Aryl groups herein include groups containing a single aromatic ring or multiple aromatic rings that are fused together, linked covalently, or linked to a common group such as a methylene or ethylene moiety. More specific aryl groups contain one aromatic ring or two or three fused or linked aromatic rings, e.g., phenyl, naphthyl, biphenyl, anthracenyl, or phenanthrenyl. In particular embodiments, aryl substituents include 1 to about 200 atoms other than hydrogen, typically 1 to about 50 atoms other than hydrogen, and specifically 1 to about 20 atoms other than hydrogen. In some embodiments herein, multi-ring moieties are substituents and in such embodiments the multi-ring moiety can be attached at an appropriate atom. For example, "naphthyl" can be 1-naphthyl or 2-naphthyl; "anthracenyl" can be 1-anthracenyl, 2-anthracenyl or 9-anthracenyl; and "phenanthrenyl" can be 1-phenanthrenyl, 2-phenanthrenyl, 3-phenanthrenyl, 4-phenanthrenyl or 9-phenanthrenyl.

The term "alkoxy" as used herein intends an alkyl group bound through a single, terminal ether linkage; that is, an "alkoxy" group may be represented as —O-alkyl where alkyl is as defined above. The term "aryloxy" is used in a similar fashion, and may be represented as —O-aryl, with aryl as defined below. The term "hydroxy" refers to —OH.

Similarly, the term "alkylthio" as used herein intends an alkyl group bound through a single, terminal thioether linkage; that is, an "alkylthio" group may be represented as —S-alkyl where alkyl is as defined above. The term "arylthio" is used similarly, and may be represented as —S-aryl, with aryl as defined below. The term "mercapto" refers to —SH.

The term "allenyl" is used herein in the conventional sense to refer to a molecular segment having the structure —CH=C=CH$_2$. An "allenyl" group may be unsubstituted or substituted with one or more non-hydrogen substituents.

The term "aryl" as used herein, and unless otherwise specified, refers to an aromatic substituent containing a single aromatic ring or multiple aromatic rings that are fused together, linked covalently, or linked to a common group such as a methylene or ethylene moiety. More specific aryl groups contain one aromatic ring or two or three fused or linked aromatic rings, e.g., phenyl, naphthyl, biphenyl, anthracenyl, phenanthrenyl, and the like. In particular embodiments, aryl substituents have 1 to about 200 carbon atoms, typically 1 to about 50 carbon atoms, and specifically 1 to about 20 carbon atoms. "Substituted aryl" refers to an aryl moiety substituted with one or more substituent groups, (e.g., tolyl, mesityl and perfluorophenyl) and the terms "heteroatom-containing aryl" and "heteroaryl" refer to aryl in which at least one carbon atom is replaced with a heteroatom (e.g., rings such as thiophene, pyridine, pyrazine, isoxazole, pyrazole, pyrrole, furan, thiazole, oxazole, imidazole, isothiazole, oxadiazole, triazole, etc. or benzo-fused analogues of these rings, such as indole, carbazole, benzofuran, benzothiophene, etc., are included in the term "heteroaryl"). In some embodiments herein, multi-ring moieties are substituents and in such an embodiment the multi-ring moiety can be attached at an appropriate atom. For example, "naphthyl" can be 1-naphthyl or 2-naphthyl; "anthracenyl" can be 1-anthracenyl, 2-anthracenyl or 9-anthracenyl; and "phenanthrenyl" can be 1-phenanthrenyl, 2-phenanthrenyl, 3-phenanthrenyl, 4-phenanthrenyl or 9-phenanthrenyl.

The terms "halo" and "halogen" are used in the conventional sense to refer to a chloro, bromo, fluoro or iodo substituent.

The terms "heterocycle" and "heterocyclic" refer to a cyclic radical, including ring-fused systems, including heteroaryl groups as defined below, in which one or more carbon atoms in a ring is replaced with a heteroatom—that is, an atom other than carbon, such as nitrogen, oxygen, sulfur, phosphorus, boron or silicon. Heterocycles and heterocyclic groups include saturated and unsaturated moieties, including heteroaryl groups as defined below. Specific examples of heterocycles include pyrrolidine, pyrroline, furan, tetrahydrofuran, thiophene, imidazole, oxazole, thiazole, indole, and the like, including any isomers of these. Additional heterocycles are described, for example, in Alan R. Katritzky, Handbook of Heterocyclic Chemistry, Pergammon Press, 1985, and in Comprehensive Heterocyclic Chemistry, A. R. Katritzky et al., eds, Elsevier, 2d. ed., 1996. The term "metallocycle" refers to a heterocycle in which one or more of the heteroatoms in the ring or rings is a metal.

The term "heteroaryl" refers to an aryl radical that includes one or more heteroatoms in the aromatic ring. Specific heteroaryl groups include groups containing heteroaromatic rings such as thiophene, pyridine, pyrazine, isoxazole, pyrazole, pyrrole, furan, thiazole, oxazole, imidazole, isothiazole, oxadiazole, triazole, and benzo-fused analogues of these rings, such as indole, carbazole, benzofuran, benzothiophene and the like.

More generally, the modifiers "hetero" or "heteroatom-containing", and "heteroalkyl" or "heteroatom-containing hydrocarbyl group" refer to a molecule or molecular fragment in which one or more carbon atoms is replaced with a heteroatom. Thus, for example, the term "heteroalkyl" refers to an alkyl substituent that is heteroatom-containing. When the term "heteroatom-containing" introduces a list of possible heteroatom-containing groups, it is intended that the term apply to every member of that group. That is, the phrase "heteroatom-containing alkyl, alkenyl and alkynyl" is to be interpreted as "heteroatom-containing alkyl, heteroatom-containing alkenyl and heteroatom-containing alkynyl."

"Hydrocarbyl" refers to hydrocarbyl radicals containing 1 to about 50 carbon atoms, specifically 1 to about 24 carbon atoms, most specifically 1 to about 16 carbon atoms, including branched or unbranched, saturated or unsaturated species, such as alkyl groups, alkenyl groups, aryl groups, and the like. The term "lower hydrocarbyl" intends a hydrocarbyl group of one to six carbon atoms, specifically one to four carbon atoms.

By "substituted" as in "substituted hydrocarbyl," "substituted aryl," "substituted alkyl," and the like, as alluded to in some of the aforementioned definitions, is meant that in the hydrocarbyl, alkyl, aryl or other moiety, at least one hydrogen atom bound to a carbon atom is replaced with one or more substituent groups such as hydroxy, alkoxy, alkylthio, phosphino, amino, halo, silyl, and the like. When the term "substituted" appears prior to a list of possible substituted groups, it is intended that the term apply to every member of that group. That is, the phrase "substituted alkyl, alkenyl and alkynyl" is to be interpreted as "substituted alkyl, substituted alkenyl and substituted alkynyl." Similarly, "optionally substituted alkyl, alkenyl and alkynyl" is to be interpreted as "optionally substituted alkyl, optionally substituted alkenyl and optionally substituted alkynyl."

The term "saturated" refers to the lack of double and triple bonds between atoms of a radical group such as ethyl, cyclohexyl, pyrrolidinyl, and the like. The term "unsaturated" refers to the presence of one or more double and triple bonds between atoms of a radical group such as vinyl, allyl, acetylide, oxazolinyl, cyclohexenyl, acetyl and the like, and specifically includes alkenyl and alkynyl groups, as well as groups in which double bonds are delocalized, as in aryl and heteroaryl groups as defined below.

By "divalent" as in "divalent hydrocarbyl", "divalent alkyl", "divalent aryl" and the like, is meant that the hydrocarbyl, alkyl, aryl or other moiety is bonded at two points to atoms, molecules or moieties with the two bonding points being covalent bonds.

As used herein the term "silyl" refers to the —$SiZ^1Z^2Z^3$ radical, where each of $Z^1$, $Z^2$, and $Z^3$ is independently selected from the group consisting of hydrogen and optionally substituted alkyl, alkenyl, alkynyl, heteroatom containing alkyl, heteroatom-containing alkenyl, heteroatom-containing alkynyl, aryl, heteroaryl, alkoxy, aryloxy, amino, silyl and combinations thereof.

As used herein the term "boryl" refers to the —$BZ^1Z^2$ group, where each of $Z^1$ and $Z^2$ is as defined above. As used herein, the term "phosphino" refers to the group —$PZ^1Z^2$, where each of $Z^1$ and $Z^2$ is as defined above. As used herein, the term "phosphine" refers to the group —$PZ^1Z^2Z^3$, where each of $Z^1$, $Z^2$, and $Z^3$ is as defined above. The term "amino" is used herein to refer to the group —$NZ^1Z^2$, where each of $Z^1$ and $Z^2$ is as defined above. The term "amine" is used herein to refer to the group —$NZ^1Z^2Z^3$, where each of $Z^1$, $Z^2$, and $Z^3$ is as defined above.

Other abbreviations used herein include: "iPr" to refer to isopropyl; "tBu" to refer to tert-butyl; "Me" to refer to methyl; "Et" to refer to ethyl; "Ph" to refer to phenyl; "Mes" to refer to mesityl (2,4,6-trimethyl phenyl); "TFA" to refer to trifluoroacetate; "THF" to refer to tetrahydrofuran; "Np" refers to napthyl; "Cbz" refers to carbazolyl; "Ant" refers to anthracenyl; and "H8-Ant" refers to 1,2,3,4,5,6,7,8-octahydroanthracenyl; "Bn" refers to benzyl; "Ac" refers to CH3CO; "EA" refers to ethyl acetate; "Ts" refers to tosyl or, synonymously, paratoluenesulfonyl; "THP" refers to tetrahydropyran; "dppf" refers to 1,1'-bis(diphenylphosphino)ferrocenel; "MOM" refers to methoxymethyl.

"Polyethylene" means a polymer made 90% ethylene-derived units, or 95% ethylene-derived units, or 100% ethylene-derived units. The polyethylene can thus be a homopolymer or a copolymer, including a terpolymer, having other monomeric units. A polyethylene described herein can, for example, include at least one or more other olefin(s) and/or comonomer(s). The olefins, for example, can contain from 3 to 16 carbon atoms in one embodiment; from 3 to 12 carbon atoms in another embodiment; from 4 to 10 carbon atoms in another embodiment; and from 4 to 8 carbon atoms in yet another embodiment. Illustrative comonomers include, but are not limited to, propylene, 1-butene, 1-pentene, 1-hexene, 1-heptene, 1-octene, 4-methylpent-1-ene, 1-decene, 1-dodecene, 1-hexadecene and the like. Also utilizable herein are polyene comonomers such as 1,3-hexadiene, 1,4-hexadiene, cyclopentadiene, dicyclopentadiene, 4-vinylcyclohex-1-ene, 1,5-cyclooctadiene, 5-vinylidene-2-norbornene and 5-vinyl-2-norbornene. Other embodiments may include ethacrylate or methacrylate.

"High molecular weight polyethylene" refers to polyethylene compositions with weight-average molecular weight of at least about $3\times10^5$ g/mol and, as used herein, is intended to include very-high molecular weight polyethylene and ultra-high molecular weight polyethylene. For purposes of the present specification, the molecular weights referenced herein are determined in accordance with the Margolies equation ("Margolies molecular weight").

"Very-high molecular weight polyethylene" refers to polyethylene compositions with a weight average molecular weight of less than about $3\times10^6$ g/mol and more than about $1\times10^6$ g/mol. In some embodiments, the molecular weight of the very-high molecular weight polyethylene composition is between about $2\times10^6$ g/mol and less than about $3\times10^6$ g/mol.

"Ultra-high molecular weight polyethylene" refers to polyethylene compositions with weight-average molecular weight of at least about $3\times10^6$ g/mol. In some embodiments, the molecular weight of the ultra-high molecular weight polyethylene composition is between about $3\times10^6$ g/mol and about $30\times10^6$ g/mol, or between about $3\times10^6$ g/mol and about $20\times10^6$ g/mol, or between about $3\times10^6$ g/mol and about $10\times10^6$ g/mol, or between about $3\times10^6$ g/mol and about $6\times10^6$ g/mol.

The term "bimodal" refers to a polymer or polymer composition, e.g., polyethylene, having a "bimodal molecular weight distribution." A "bimodal" composition can include a polyethylene component with at least one identifiable higher molecular weight and a polyethylene component with at least one identifiable lower molecular weight, e.g., two distinct peaks on an SEC curve (GPC chromatogram). A material with more than two different molecular weight distribution peaks will be considered "bimodal" as that term is used although the material may also be referred to as a "multimodal" composition, e.g., a trimodal or even tetramodal, etc. composition.

The term "broad" as in "broad molecular weight distribution" includes the case where a polyethylene composition is comprised of a blend of higher and lower molecular weight components but where there are not two distinct peaks on an SEC curve (GPC chromatogram), but rather a single peak which is broader than the individual component peaks.

"Ultra-high molecular weight polyethylene component" refers to a polyethylene component in a bimodal (or multimodal) composition with a weight average molecular weight of at least about $3\times10^6$ g/mol. In some embodiments, the ultrahigh molecular weight polyethylene component has a weight average molecular weight between about $3\times10^6$ g/mol and about $20\times10^6$ g/mol, or between about $3\times10^6$ g/mol and about $15\times10^6$ g/mol, or between about $3\times10^6$ g/mol and about $10\times10^6$ g/mol, or between about $3\times10^6$ g/mol and about $6\times10^6$ g/mol. When the composition includes more than two components, e.g., a trimodal composition, the multimodal composition may have more than one ultra-high molecular weight component.

"Very-high molecular weight polyethylene component" refers to a polyethylene component in a bimodal (or multimodal) composition with a weight average molecular weight of less than about $3\times10^6$ g/mol (e.g., less than about $2.75\times10^6$ g/mol, about $2.5\times10^6$ g/mol, about $2.25\times10^6$ g/mol, or even about $2\times10^6$ g/mol) and more than about $1\times10^6$ g/mol (e.g., more than about $1.5\times10^6$ g/mol, or about $2\times10^6$ g/mol).

Ligands

The ligands employed in the catalyst used in the present process can generally be defined as phenolate ether ligands and more particularly bis(phenolate) ether ligands. For example, the ligands suitable for use in the may be characterized by the following general formula:

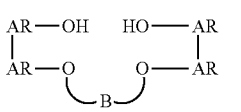

(I)

wherein each ligand has at least two hydrogen atoms capable of removal in a binding reaction with a metal atom or metal precursor or base; AR is an aromatic group that can be the same as or different from the other AR groups with, generally, each AR being independently selected from the group consisting of optionally substituted aryl or optionally substituted heteroaryl; and B is a bridging group having from 3 to 50 atoms (not counting hydrogen atoms). In one preferred embodiment, B is a bridge of between about 3 and about 20 carbon atoms (not including hydrogen atoms).

Generally, the "upper aromatic ring" is the ring to which the hydroxyls are bonded or part of. Similarly, the "lower aromatic ring" is the ring to which the oxygens are bonded or part of. In some embodiments, AR-AR (that is, the structure formed from one upper aromatic ring and its corresponding lower aromatic ring) is a biaryl species, more specifically a biphenyl.

In some embodiments, the bridging group B is selected from the group consisting of divalent hydrocarbyl and divalent heteroatom containing hydrocarbyl (including, for example, between about 3 and about 20 carbon atoms), which may be optionally substituted. In more particular embodiments, B is selected from the group consisting of optionally substituted divalent alkyl, alkenyl, alkynyl, heteroalkyl, heteroalkenyl, heteroalkynyl, aryl, heteroaryl and silyl. In any of these embodiments, the bridging group can be substituted with one or more optionally substituted hydrocarbyl or optionally substituted heteroatom-containing hydrocarbyl groups, such as optionally substituted alkyl, alkenyl, alkynyl, heteroalkyl, heteroalkenyl, heteroalkynyl, aryl, or heteroaryl. It should be noted that these substitutions are in addition to the bonds between the bridging group B and the oxygen atoms in formula I. Two or more of the hydrocarbyl or heteroatom-containing hydrocarbyl groups can be joined into a ring structure having from 3 to 50 atoms in the ring structure (not counting hydrogen atoms). In some embodiments in which the bridging group includes one or more ring structures, it may be possible to identify more than one chain of bridge atoms extending from the oxygen atoms, and in such cases it can be convenient to define the "bridge" as the shortest path of connectivity between the oxygen atoms, and the "substituents" as the groups bonded to atoms in the bridge. Where there are two alternative, equally short paths of connectivity, the bridge can be defined along either path.

In still other embodiments, B can be represented by the general formula -(Q"$R^{40}_{2-z"}$)$_{z'}$— wherein each Q" is independently either carbon or silicon and where each $R^{40}$ is independently selected from the group consisting of hydrogen and optionally substituted hydrocarbyl or optionally substituted heteroatom containing hydrocarbyl. Two or more $R^{40}$ groups may be joined into a ring structure having from 3 to 50 atoms in the ring structure (not counting hydrogen atoms). In these embodiments, z' is an integer from 1 to 10, more specifically from 1 to 5 and even more specifically from 2-5, and z" is 0, 1 or 2. For example, when z" is 2, there is no $R^{40}$ group associated with Q", which allows for those cases where one Q" is multiply bonded to a second Q". In more specific embodiments, $R^{40}$ is selected from the group consisting of hydrogen, halogen, and optionally substituted alkyl, alkenyl, alkynyl, heteroalkyl, heteroalkenyl, heteroalkynyl, aryl, heteroaryl, alkoxyl, aryloxyl, silyl, boryl, phosphino, amino, alkylthio, arylthio, and combinations thereof, where at least one $R^{40}$ group in B is not hydrogen. In any of the embodiments mentioned above, the B group can include one or more chiral centers. Thus, for example, B can be represented by the formula —CHR$^{50}$—(CH$_2$)$_m$—CHR$^{51}$—, where $R^{50}$ and $R^{51}$ are independently selected from the group consisting of optionally substituted alkyl, heteroalkyl, aryl or heteroaryl, $R^{50}$ and $R^{51}$ can be arranged in any relative configuration (e.g., syn/anti, threo/erythro, or the like), and where the ligand can be generated as a racemic mixture or in an enantiomerically pure form.

In particular embodiments, the bridging group B includes a chain of one or more bridge atoms extending from the oxygen atoms and one or more of the bridge atoms situated adjacent to one or both of the oxygen atoms is bonded to one or more substituents (not counting bonds to one or both of the oxygen atoms or neighboring bridge atoms along the chain, as noted above), where the substituents are independently selected from the group consisting of optionally substituted alkyl, heteroalkyl, aryl and heteroaryl. In more particular embodiments, the bridging group B is substituted with a plurality of substituents that are independently selected from the group consisting of optionally substituted alkyl, heteroalkyl, aryl and heteroaryl, such that each of the bridge atoms that is adjacent to one or both of the oxygen atoms is bonded to at least one substituent, again not counting bonds to the oxygen atoms or neighboring bridge atoms. In such embodiments, two or more of the substituents can be joined into a ring structure having from 3 to 50 atoms in the ring structure (not counting hydrogen atoms).

Thus, in some embodiments, the O—B—O fragment can be characterized by one of the following formulae:

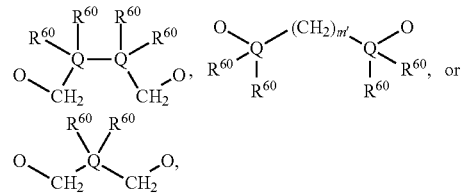

where each Q is independently selected from the group consisting of carbon and silicon, each $R^{60}$ is independently selected from the group consisting of hydrogen and optionally substituted hydrocarbyl and heteroatom containing hydrocarbyl, provided that at least one $R^{60}$ substituent is not hydrogen, wherein the $R^{60}$ substituents are optionally joined into a ring structure having from 3 to 50 atoms in the ring structure not counting hydrogen atoms, and m' is 0, 1, 2 or 3. Specific O—B—O fragments within these embodiments include, for example, O—(CH$_2$)$_3$—O, O—(CH$_2$)$_4$—O, O—CH(CH$_3$)—CH(CH$_3$)—O, O—CH$_2$—CH(CH$_3$)—CH$_2$—O, O—CH$_2$—C(CH$_3$)$_2$—CH$_2$—O, O—CH$_2$—CH(CHMe$_2$)—CH$_2$—O, O—CH$_2$—CH(C$_6$H$_5$)—CH$_2$—O, O—CH(CH$_3$)—CH$_2$—CH(CH$_3$)—O, O—CH(C$_2$H$_5$)—CH$_2$—CH(C$_2$H$_5$)—O, O—CH(CH$_3$)CH$_2$CH$_2$CH(CH$_3$)—O, O—CH(C$_6$H$_5$)CH$_2$CH(C$_6$H$_5$)—O,

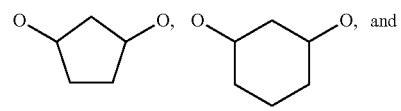

and

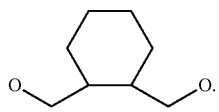

Other specific bridging moieties are set forth in the example ligands and complexes herein.

In particular embodiments, the ligands can be characterized by the general formula:

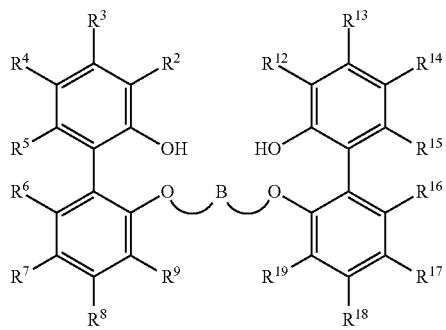

(II)

wherein each of $R^2$, $R^3$, $R^4$, $R^5$, $R^6$, $R^7$, $R^8$, $R^9$, $R^{12}$, $R^{13}$, $R^{14}$, $R^{15}$, $R^{16}$, $R^{17}$, $R^{18}$, and $R^{19}$ is independently selected from the group consisting of hydrogen, halogen, and optionally substituted hydrocarbyl, heteroatom-containing hydrocarbyl, alkoxy, aryloxy, silyl, boryl, phosphino, amino, alkylthio, arylthio, nitro, and combinations thereof; optionally two or more R groups can combine together into ring structures (for example, single ring or multiple ring structures), with such ring structures having from 3 to 12 atoms in the ring (not counting hydrogen atoms); and B is a bridging group as defined above.

In more specific embodiments, $R^2$, $R^3$, $R^4$, $R^5$, $R^6$, $R^7$, $R^8$, $R^9$, $R^{12}$, $R^{13}$, $R^{14}$, $R^{15}$, $R^{16}$, $R^{17}$, $R^{18}$, and $R^{19}$ is independently selected from the group consisting of hydrogen, halogen, and optionally substituted alkyl, heteroalkyl, aryl, heteroaryl, alkoxyl, aryloxyl, silyl, amino, alkylthio and arylthio. In some embodiments, at least one of $R^2$ and $R^{12}$ is not hydrogen and in still other embodiments both $R^2$ and $R^{12}$ are not hydrogen.

In more specific embodiments, $R^2$ and $R^{12}$ are selected from the group consisting of an aryl and a heteroaryl (e.g., phenyl, substituted phenyl, antrazenyl carbozyl, mesityl, 3,5-(t-Bu)-2-phenyl and the like); $R^3$, $R^4$, $R^5$, $R^6$, $R^7$, $R^8$, $R^9$, $R^{13}$, $R^{14}$, $R^{15}$, $R^{16}$, $R^{17}$, $R^{18}$, and $R^{19}$ are defined as above; and B is:

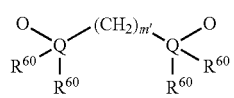

wherein Q, $R^{60}$, and m' are as defined above.

In another specific embodiment, $R^2$ and $R^{12}$ are independently selected from the group consisting of substituted or unsubstituted moieties of the general formulae:

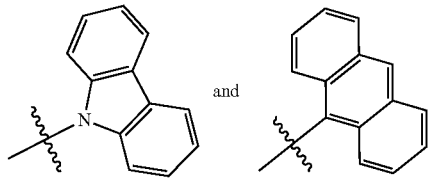

wherein the denoted broken bonds are points of attachment to the remaining portion of the molecule; $R^4$ and $R^{14}$ are each an alkyl; $R^3$, $R^5$, $R^6$, $R^7$, $R^8$, $R^9$, $R^{13}$, $R^{15}$, $R^{16}$, $R^{17}$, $R^{18}$, and $R^{19}$ are hydrogen, and B is selected from the group consisting of:

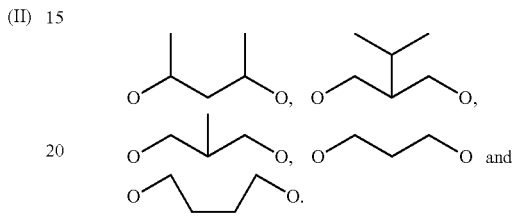

The illustrated structures are provided for purposes of illustration and should not be viewed in a limiting sense. For example, one or more of the rings may be substituted with one of more substituents selected from, for example, Me, iPr, Ph, Bn, tBu, and the like.

In more specific embodiments, the ligands can be characterized by the formula:

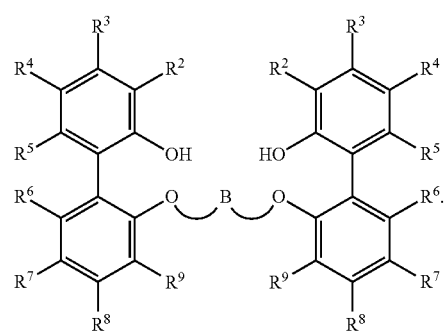

(III)

In formula III, each of $R^2$, $R^3$, $R^4$, $R^5$, $R^6$, $R^7$, $R^8$ and $R^9$ is independently selected from the group consisting of hydrogen, halogen, and optionally substituted alkyl, alkenyl, alkynyl, heteroalkyl, heteroalkenyl, heteroalkynyl, aryl, heteroaryl, alkoxyl, aryloxyl, silyl, boryl, phosphino, amino, mercapto, alkylthio and arylthio, nitro, and combinations thereof. The remaining substituent B is defined as above.

In more specific embodiments, $R^2$ is selected from the group consisting of an aryl and a heteroaryl; $R^4$ is alkyl; $R^3$, $R^5$, $R^6$, $R^7$, $R^8$, $R^9$ are hydrogen; and B is:

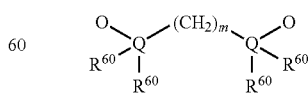

wherein Q, $R^{60}$, and m' are as defined above.

In another particular embodiment, $R^2$ is selected from the group consisting of substituted or unsubstituted moieties of the general formulae:

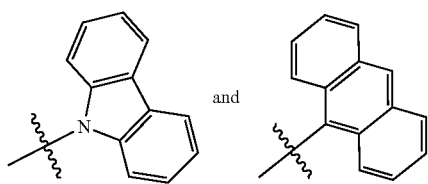

$R^4$ is alkyl; $R^3$, $R^5$, $R^6$, $R^7$, $R^8$, $R^9$ are defined as above; and B is selected from the group consisting of:

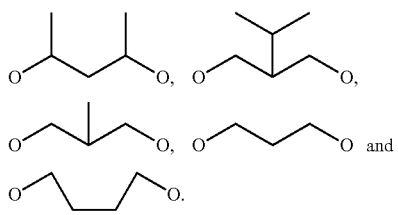

In one embodiment, the ligands are selected from the group consisting of the structures illustrated below:

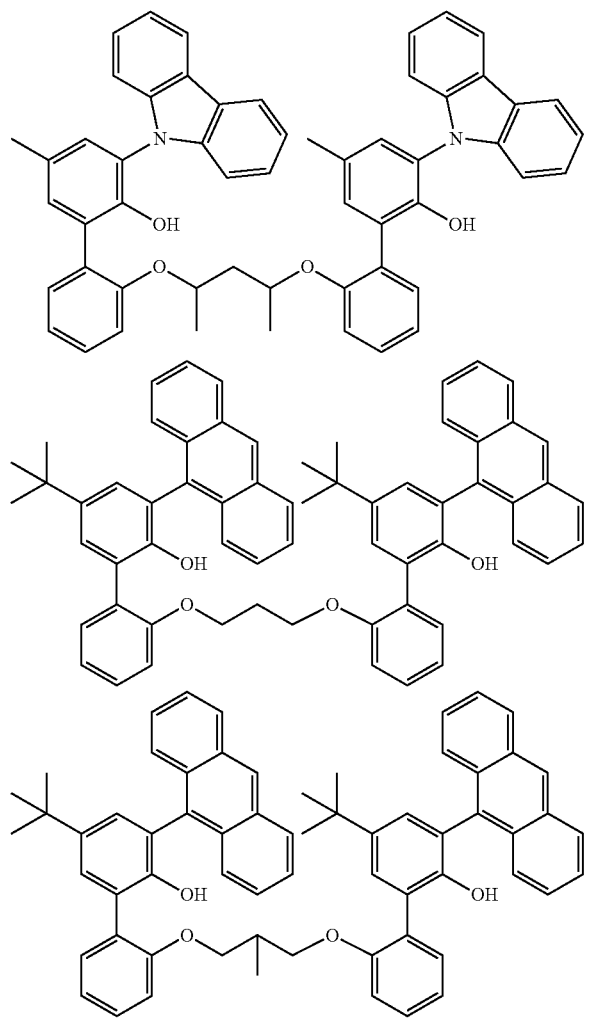

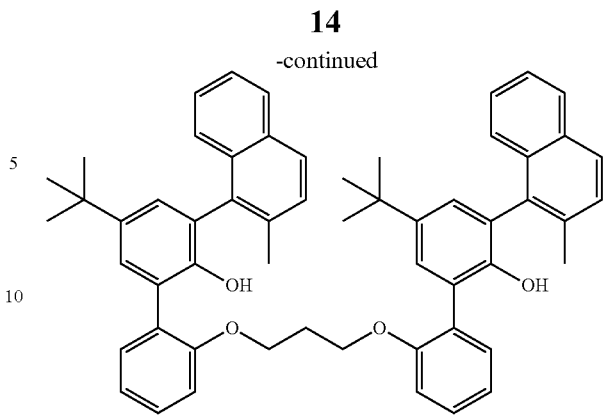

Ligand Preparation

Generally speaking, the ligands disclosed herein be prepared using known procedures, such as those described, for example, in March, Advanced Organic Chemistry, Wiley, New York 1992 (4th Ed.). More specifically, the ligands of the invention can be prepared using a variety of synthetic routes, depending on the variation desired in the ligand. In general, the ligands are prepared in a convergent approach by preparing building blocks that are then linked together either directly or with a bridging group. Variations in the R group substituents can be introduced in the synthesis of the building blocks. Variations in the bridge can be introduced with the synthesis of the bridging group. The preparation of suitable ligands has also been described in detail in, for example, WO 03/091262, WO 2005/0084106, U.S. Pat. No. 7,060,848, U.S. Pat. No. 7,091,292, U.S. Pat. No. 7,126,031, U.S. Pat. No. 7,241,714, U.S. Pat. No. 7,241,715, and U.S. Patent Publication No. 2008/0269470; the entire contents of which are incorporated herein by reference.

Metal Precursor Compounds

Once the desired ligand is formed, it may be combined with a metal atom, ion, compound or other metal precursor compound. For example, in some embodiments, the metal precursors are activated metal precursors, which refers to a metal precursor (described below) that has been combined or reacted with an activator (described below) prior to combination or reaction with the ancillary ligand. In some applications, the ligands are combined with a metal compound or precursor and the product of such combination is not determined, if a product forms. For example, the ligand may be added to a reaction vessel at the same time as the metal or metal precursor compound along with the reactants, activators, scavengers, etc. Additionally, the ligand can be modified prior to addition to or after the addition of the metal precursor, e.g. through a deprotonation reaction or some other modification.

In general, the metal precursor compounds may be characterized by the general formula M(L)n where M is a metal selected from Group 4 of the Periodic Table of Elements, more specifically from Hf and Zr, especially Zr. Each L is a ligand independently selected from the group consisting of hydrogen, halogen, optionally substituted alkyl, heteroalkyl, allyl, diene, alkenyl, heteroalkenyl, alkynyl, heteroalkynyl, aryl, heteroaryl, alkoxy, aryloxy, boryl, silyl, amino, phosphino, ether, thioether, phosphine, amine, carboxylate, alkylthio, arylthio, 1,3-dionate, oxalate, carbonate, nitrate, sulfate, and combinations thereof. Optionally, two or more L groups are joined into a ring structure. One or more of the ligands L may also be ionically bonded to the metal M and, for example, L may be a noncoordinated or loosely coordinated or weakly coordinated anion (e.g., L may be selected from the group consisting of those anions described below in the conjunction with the activators); and optionally two or more L groups may be linked together in a ring structure. (See, e.g., Marks et al., Chem. Rev. 2000, 100, 1391-1434 for a detailed discussion of these weak interactions.) The subscript n is 1, 2, 3, 4, 5, or 6. The metal precursors may be monomeric, dimeric or higher orders thereof.

Specific examples of suitable hafnium and zirconium precursors include, but are not limited: $HfCl_4$, $Hf(CH_2Ph)_4$, $Hf(CH_2CMe_3)_4$, $Hf(CH_2SiMe_3)_4$, $Hf(CH_2Ph)_3Cl$, $Hf(CH_2CMe_3)_3Cl$, $Hf(CH_2SiMe_3)_3Cl$, $Hf(CH_2Ph)_2Cl_2$, $Hf(CH_2CMe_3)_2Cl_2$, $Hf(CH_2SiMe_3)_2Cl_2$, $Hf(NMe_2)_4$, $Hf(NEt_2)_4$, $Hf(N(SiMe_3)_2)_2Cl_2$, $Hf(N(SiMe_3)CH_2CH_2CH_2N(SiMe_3))Cl_2$, and, $Hf(N(Ph)CH_2CH_2CH_2N(Ph))Cl_2$, as well as $ZrCl_4$, $Zr(CH_2Ph)_4$, $Zr(CH_2CMe_3)_4$, $Zr(CH_2SiMe_3)_4$, $Zr(CH_2Ph)_3Cl$, $Zr(CH_2CMe_3)_3Cl$, $Zr(CH_2SiMe_3)_3Cl$, $Zr(CH_2Ph)_2Cl_2$, $Zr(CH_2CMe_3)_2Cl_2$, $Zr(CH_2SiMe_3)_2Cl_2$, $Zr(NMe_2)_4$, $Zr(NEt_2)_4$, $Zr(NMe_2)_2Cl_2$, $Zr(NEt_2)_2Cl_2$, $Zr(N(SiMe_3)_2)_2Cl_2$, $Zr(N(SiMe_3)CH_2ZrCH_2CH_2N(SiMe_3))Cl_2$, and $Zr(N(Ph)CH_2CH_2CH_2N(Ph))Cl_2$. Lewis base adducts of these examples are also suitable as metal precursors, for example, ethers, amines, thioethers, phosphines and the like are suitable as Lewis bases. Specific examples include $MCl_4(THF)_2$, $MCl_4(SMe_2)_2$ and $M(CH_2Ph)_2Cl_2(OEt_2)$ where M=Zr or Hf. Activated metal precursors may be ionic or zwitterionic compounds, such as $[M(CH_2Ph)_3^+][B(C_6F_5)_4^-]$ or $[M(CH_2Ph)_3^+][PhCH_2B(C_6F_5)_3^-]$ where M is Zr or Hf. Activated metal precursors or such ionic compounds can be prepared in the manner shown in Pellecchia et al., Organometallics, 1994, 13, 298-302; Pellecchia et al., J. Am. Chem. Soc., 1993, 115, 1160-1162; Pellecchia et al., Organometallics, 1993, 13, 3773-3775 and Bochmann et al., Organometallics, 1993, 12, 633-640, each of which is incorporated herein by reference.

The ligand to metal precursor compound ratio is typically in the range of about 0.1:1 to about 10:1, or about 0.5:1 to about 5:1, or about 0.75:1 to about 2.5:1, and more specifically about 1:1.

As also noted above, in another aspect the invention relates to metal-ligand complexes. Generally, the ligand (or optionally a modified ligand as discussed above) is mixed with a suitable metal precursor (and optionally other components, such as activators) prior to or simultaneously with allowing the mixture to be contacted with the reactants (e.g., monomers). When the ligand is mixed with the metal precursor compound, a metal-ligand complex may be formed, which may be supported with an appropriate activator to form a supported catalyst (or co-supported catalyst) suitable for use in accordance with the present invention.

Metal-Ligand Complexes

The metal-ligand complexes according to the invention, which may be supported with an activator to form a catalyst of the present invention, can in general be described in a number of overlapping or alternative ways. Thus, the metal-ligand complexes can be described as complexes having dianionic, chelating ligands that may occupy up to four coordination sites of the metal atom. The metalligand complexes can also be described as having dianionic ligands that form two seven-member metallocycles with the metal atom (counting the metal atom as one member of the seven member ring). Also, in some embodiments, the metal-ligand complexes can be described as having dianionic, chelating ligands that use oxygen as binding atoms to the metal atom.

Also, in some embodiments, the metal-ligand complexes can be described as having ligands that can coordinate in at least two approximate $C_2$ symmetric complex isomers. By approximate $C_2$ symmetry it is meant that the ligand coordinates with a metal such that the ligand parts occupy four quadrants around the metal center extending towards the ligands L in an approximate $C_2$ symmetric fashion, and approximate means that true symmetry may not exist due to several factors that effect symmetry, including, for example, the effect of the bridge. In these embodiments, the conformation of the ligand around the metal can be described as lambda or delta. At least two isomeric complexes can be formed which may be enantiomeric or diastereomeric to each other. For ligands containing one or more chiral centers (e.g., substituted bridges with chiral centers), diastereomeric metalligand complexes can be formed. The diastereomeric complexes formed by a particular ligand-metal precursor combination can be used as mixtures of diastereomers, or can be separated and used as diastereomerically-pure complexes.

These isomeric structures may be separately formed by employing suitable metal precursors containing appropriately substituted ligands (such as chelating bis-amide, bis-phenol, or diene ligands, as described below), which may strongly influence the stereochemistry of complexation reactions. It is known that group 4 metal complexes containing chelating ligands can be used as metal precursors in complexation reactions with the bridged bis-cyclopentadienyl ligands to control the stereochemistry of the resulting bridged metallocene complex, as is described in Zhang et al., J. Am. Chem. Soc., 2000; 122, 8093-8094, LoCoco et al., Organometallics, 2003, 22, 5498-5503, and Chen et al., J. Am. Chem. Soc., 2004, 126, 42-43. The use of analogous Group 4 metal precursors containing appropriately substituted chelating ligands in complexation reactions with the bridged bis(biaryl) ligands described herein may provide a mechanism to influence the stereochemistry of the resulting chiral approximately C2-symmetric metal-ligand complexes. The use of analogous chiral Group 4 metal precursors containing appropriately substituted chelating ligands that possess one or more chiral centers may provide a mechanism to influence the absolute stereochemistry of the resulting chiral approximately C2-symmetric metal-ligand complexes. The use of substantially enantiomerically pure Group 4 metal precursors containing appropriately substituted chelating ligands that possess one or more chiral centers may provide a mechanism to prepare substantially enantiomerically or diastereomerically pure approximately C2-symmetric metal-ligand complexes of this invention.

In some cases, it may also be possible to separate mixtures of enantiomers or diastereomers by means of diastereomeric/enantiomeric resolution using a chiral reagent. See, for example, Ringwald et al., J. Am. Chem. Soc., 1999, 121, pp. 1524-1527.

The various diastereomeric complexes may have different polymerization performance when used as catalysts for polymerizations, resulting, for example, in the formation of polymer products having bimodal molecular weight and/or composition distribution.

In one embodiment, metal-ligand complexes used in the present catalyst may be characterized by the general formula:

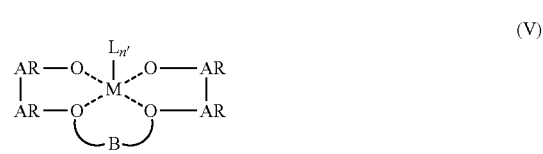

(V)

wherein each of AR, M, L, B, and n', are as defined above; and the dotted lines indicate possible binding to the metal atom, provided that at least two of the dotted lines are covalent bonds.

In this regard it is to be noted that Ln' indicates that the metal M is bonded to a number n' groups of L, as defined above.

It is to be further noted that, in one preferred embodiment, B is a bridge of between about 3 and about 50 carbon atoms (not including hydrogen atoms), and more preferably is a bridge of between about 3 and about 20 carbon atoms.

More particularly, the metal-ligand complex used herein can be characterized by the general formula:

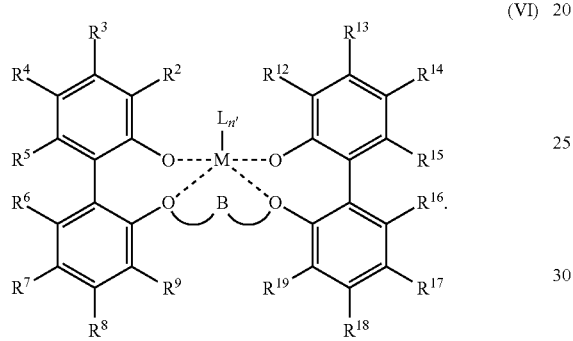

(VI)

wherein each of $R^2$, $R^3$, $R^4$, $R^5$, $R^6$, $R^7$, $R^8$, $R^9$, $R^{12}$, $R^{13}$, $R^{14}$, $R^{15}$, $R^{16}$, $R^{17}$, $R^{18}$, and $R^{19}$ are as defined above for structure (II), and M, L, n', B, are as defined above and as further explained in connection with structure (V). The dotted lines indicate possible binding to the metal atom, provided that at least two of the dotted lines are covalent bonds.

Specific examples of suitable metal-ligand complexes include:

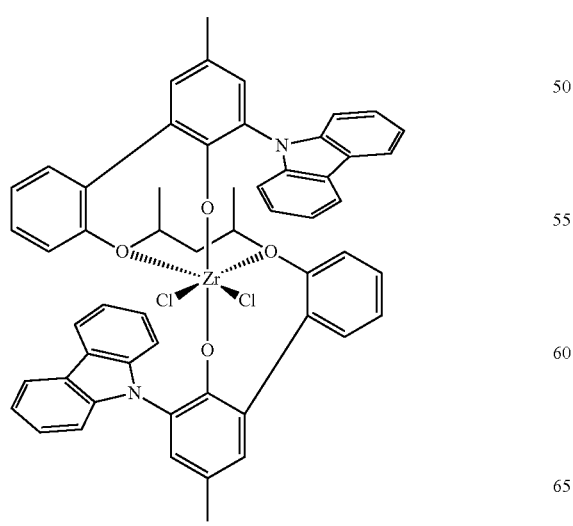

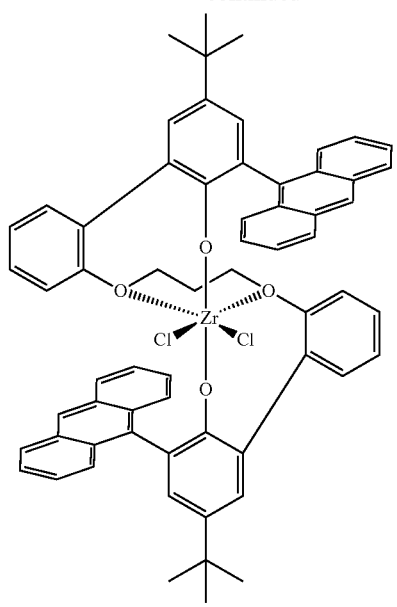

-continued

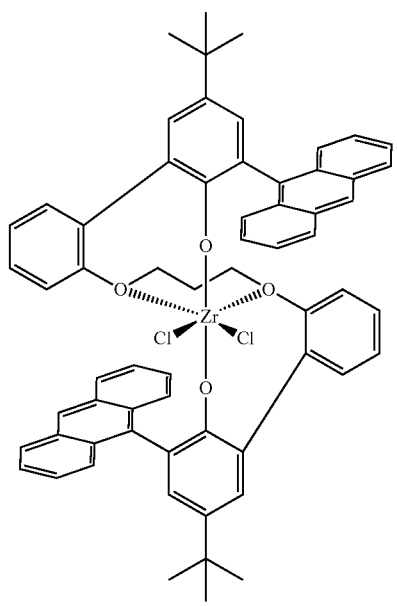

-continued

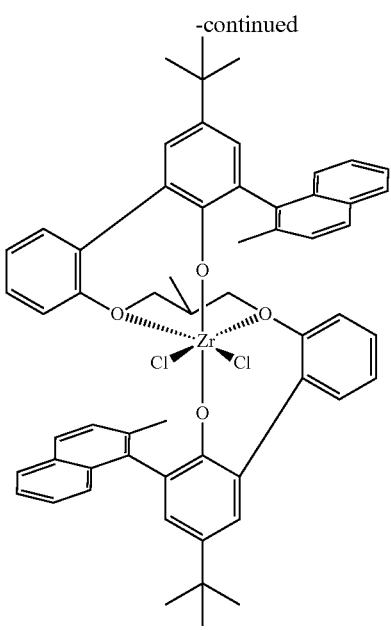

Metal-Ligand Complex Preparation

The metal-ligand complexes can be formed by techniques known to those of skill in the art, such as combinations of metal precursors and ligands under conditions to afford complexation. For example, the complexes of this invention can be prepared according to the general scheme shown below:

Scheme 13

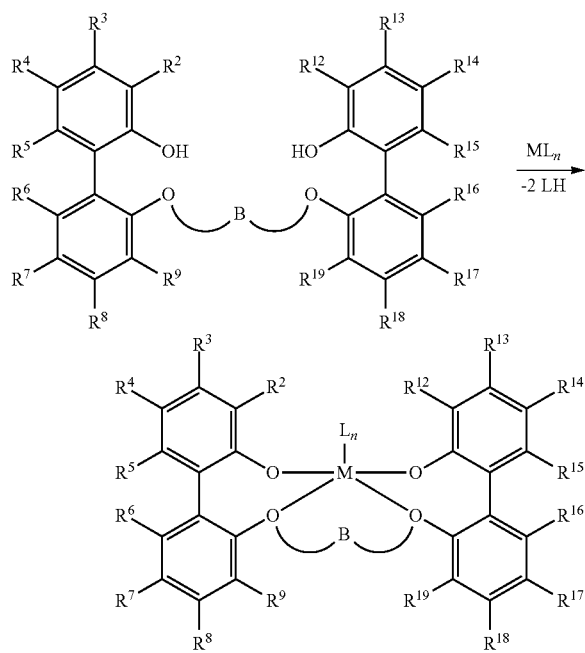

As shown in Scheme 13, a ligand according to formula II is combined with the metal precursor M(L)n under conditions to cause the removal of at least 2 leaving group ligands L, which are shown in the scheme as combining with a hydrogen (H). Other schemes where the leaving group ligand combines with other moieties (e.g., Li, Na, etc.) employing other known routes for complexation can be used, including for example, reactions where the ligand L reacts with other moieties (e.g., where the alkali metal salt of the ligand is used and the complexation reaction proceeds by salt elimination).

Catalyst Support

The metal-ligand complex described above is supported on a particulate support in order to obtain the supported catalyst used in the present process. Suitable supports include silicas, aluminas, clays, zeolites, magnesium chloride, polystyrenes, substituted polystyrenes and the like. Inorganic oxide supports and especially silica supports are normally preferred.

It is often desirable to ensure that the average particle size, d50, of the support is less than 58 microns and generally less than 50 microns, for example less than 30 microns, such as about 4 to about 20 microns. Thus, it is generally found that, by controlling the particle size of the support within the above limits, the activity of the catalyst is improved. Also the particle size and form of the support influences the size and form of the polymer particle that is produced with a given support.

In addition, it is in some cases desirable that the support particles have a span, $\log_{10}(d_{90}/d_{10})$ less than 0.6.

Prior to loading the metal-ligand complex, the support is generally treated with an activator (such as one or more of the activators described below) and especially with an organoaluminum compound, such as an alumoxane, for example methyl alumoxane (MAO). In some cases it is preferred to use PMAO-IP to treat the support. Such treatment can include calcination of the support at a suitable temperature, say, from about 500° to about 900° C., e.g., about 600°, preferably in a non-oxidizing environment, e.g., nitrogen. The calcined product can then be slurried with a suitable diluent, e.g., a liquid hydrocarbon, such as heptane, to which a source of activating material is added, and heated to about 50° C. After removing the diluent and drying, a treated support is obtained suitable for receiving the metal-ligand complex.

Loading the metal-ligand complex on the treated support is generally achieved by slurrying the support in a suitable liquid hydrocarbon, and adding, with suitable agitation e.g. vortexing, the metal complex in a suitable solvent under a protective atmosphere of dry inert gas, e.g. nitrogen or argon, for about 1 to about 3 hours.

In one embodiment, the loading of the metal-ligand complex deposited on the support is from about 1 μmol/gram of supported catalyst to about 100 μmol/gram of supported catalyst. In another embodiment, the loading is from about 2 μmol/gram of supported catalyst to about 100 μmol/gram of supported catalyst and, in another embodiment, from about 4 μmol/gram of supported catalyst to about 100 μmol/gram of supported catalyst. In another embodiment, the loading of the metal-ligand complex deposited on the support is from about 1 μmol/gram of supported catalyst to about 50 μmol/gram of supported catalyst. In another embodiment, the loading is from about 2 μmol/gram of supported catalyst to about 50 μmol/gram of supported catalyst and, in another embodiment, from about 4 μmol/gram of supported catalyst to about 50 μmol/gram of supported catalyst. In other embodiments, the loading of the metal-ligand complex deposited on the support is from about 1 μmol/gram of supported catalyst to about 25 μmol/gram of supported catalyst, from about 2 μmol/gram of supported catalyst to about 25 μmol/gram of supported catalyst or from about 4 μmol/gram of supported catalyst to about 25 μmol/gram of supported catalyst. In other embodiments, the loading of the metalligand complex deposited on the support is from about 1 μmol/gram of supported catalyst to about 20 μmol/gram of supported catalyst, from about 2 μmol/gram of supported catalyst to about 20 μmol/gram of supported catalyst or from about 4 μmol/gram of supported catalyst to about 20 μmol/gram of supported catalyst. In further embodiments, the loading of the metal-ligand complex deposited on the support is from about 1 µmol/gram of supported catalyst to about 15 µmol/gram of supported catalyst, from about 2 µmol/gram of supported catalyst to about 15 µmol/gram of supported catalyst or from about 4 µmol/gram of supported catalyst to about 15 µmol/gram of supported catalyst. In additional embodiments, the loading of the metal-ligand complex deposited on the support is from about 1 µmol/gram of supported catalyst to about 10 µmol/gram of supported catalyst, from about 2 µmol/gram of supported catalyst to about 10 µmol/gram of supported catalyst or even from about 3 µmol/gram of supported catalyst to about 10 µmol/gram of supported catalyst. In other embodiments, the loading of the metal-ligand complex deposited on the support is about 1 µmol/gram of supported catalyst, about 2 µmol/gram, about 4 µmol/gram, about 10 µmol/gram, about 20 µmol/gram, about 30 µmol/gram, about 40 µmol/gram, about 50 µmol/gram or even about 100 µmol/gram.

Two different metal-ligand complexes may be deposited on the organic or inorganic support to form a two component co-supported catalyst. Such two component catalysts are particularly useful for the production of bimodal ultra-high molecular weight polyethylene. In one embodiment, the total loading of the two metal-ligand complexes deposited on the support is from about 1 µmol/gram of supported catalyst to about 100 µmol/gram of supported catalyst. In another embodiment, the total loading of the metal-ligand complexes deposited on the support is from about 2 µmol/gram of supported catalyst to about 100 µmol/gram of supported catalyst and, in another embodiment, from about 4 µmol/gram of supported catalyst to about 100 µmol/gram of supported catalyst. In one embodiment, the total loading of the two metal-ligand complexes deposited on the support is from about 1 µmol/gram of supported catalyst to about 50 µmol/gram of supported catalyst. In another embodiment, the total loading of the metal-ligand complexes deposited on the support is from about 2 µmol/gram of supported catalyst to about 50 µmol/gram of supported catalyst and, in another embodiment, from about 4 µmol/gram of supported catalyst to about 50 µmol/gram of supported catalyst. In further embodiments, the loading of the metal-ligand complexes deposited on the support is from about 1 µmol/gram of supported catalyst to about 25 µmol/gram of supported catalyst, from about 2 µmol/gram of supported catalyst to about 25 µmol/gram of supported catalyst or from about 4 µmol/gram of supported catalyst to about 25 µmol/gram of supported catalyst. In other embodiments, the loading of the metal-ligand complexes deposited on the support is from about 1 µmol/gram of supported catalyst to about 20 µmol/gram of supported catalyst, from about 2 µmol/gram of supported catalyst to about 20 µmol/gram of supported catalyst or from about 4 µmol/gram of supported catalyst to about 20 µmol/gram of supported catalyst. In additional embodiments, the loading of the metal-ligand complexes deposited on the support is from about 1 µmol/gram of supported catalyst to about 10 µmol/gram of supported catalyst, from about 2 µmol/gram of supported catalyst to about 10 µmol/gram of supported catalyst or even from about 4 µmol/gram of supported catalyst to about 10 µmol/gram of supported catalyst. In other embodiments, the loading of the metal-ligand complexes deposited on the support is about 1 µmol/gram of supported catalyst, about 2 µmol/gram, about 4 µmol/gram, about 10 µmol/gram, about 20 µmol/gram, about 30 µmol/gram, about 40 µmol/gram, about 50 µmol/gram or even about 100 µmol/gram.

When two metal-ligand complexes are deposited on the support, the molar ratio of the first complex to the second complex may be about 1:1, or alternatively the supported two-component complex may include a molar excess of one of the complexes relative to the other. For example, the ratio of the first complex to the second complex may be about 1:2; about 1:3; about 1:5; about 1:10; about 1:20 or more. In one embodiment, the ratio of the first metal-ligand complex to the second metal-ligand complex deposited on the support is between about 1:1 and 1:10 and in another embodiment between about 1:1 to about 1:5. Further, the ratio may be adjusted as needed and may be determined experimentally in order to obtain a bimodal composition with a target split between the high molecular weight component and the low molecular weight polyethylene component.

Activators for the Metal-Ligand Complexes

The metal-ligand complexes described above are active polymerization catalysts when combined with one or more suitable activators. Broadly, the activator(s) may comprise alumoxanes, Lewis acids, Bronsted acids, compatible non-interfering activators and combinations of the foregoing. These types of activators have been taught for use with different compositions or metal complexes in the following references, which are hereby incorporated by reference in their entirety: U.S. Pat. No. 5,599,761, U.S. Pat. No. 5,616,664, U.S. Pat. No. 5,453,410, U.S. Pat. No. 5,153,157, U.S. Pat. No. 5,064,802, EP-A-277,004 and Marks et al., Chem. Rev. 2000, 100, 1391-1434. In some embodiments, ionic or ion forming activators are preferred. In other embodiments, alumoxane activators are preferred.

Suitable ion forming compounds useful as an activator in one embodiment comprise a cation that is a Bronsted acid capable of donating a proton, and an inert, compatible, non-interfering, anion, A–. Suitable anions include, but are not limited to, those containing a single coordination complex comprising a charge-bearing metal or metalloid core. Mechanistically, the anion should be sufficiently labile to be displaced by olefinic, diolefinic and unsaturated compounds or other neutral Lewis bases such as ethers or nitriles. Suitable metals include, but are not limited to, aluminum, gold and platinum. Suitable metalloids include, but are not limited to, boron, phosphorus, and silicon. Compounds containing anions that comprise coordination complexes containing a single metal or metalloid atom are, of course, well known and many, particularly such compounds containing a single boron atom in the anion portion, are available commercially.

Specifically, such activators may be represented by the following general formula:

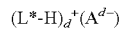

$(L^*-H)_d^+(A^{d-})$ wherein L* is a neutral Lewis base; (L*-H)+ is a Bronsted acid; $A^{d-}$ is a noninterfering, compatible anion having a charge of d–, and d is an integer from 1 to 3. More specifically $A^{d-}$ corresponds to the formula: $(M'^{3+}Q_h)^{d-}$ wherein h is an integer from 4 to 6; h–3=d; M' is an element selected from Group 13 of the Periodic Table; and Q is independently selected from the group consisting of hydrogen, dialkylamido, halogen, alkoxy, aryloxy, hydrocarbyl, and substituted-hydrocarbyl radicals (including halogen substituted hydrocarbyl, such as perhalogenated hydrocarbyl radicals), said Q having up to 20 carbons. In a more specific embodiment, d is one, i.e., the counter ion has a single negative charge and corresponds to the formula A–.

Activators comprising boron or aluminum can be represented by the following general formula:

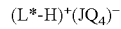

$(L^*-H)^+(JQ_4)^-$ wherein: L* is as previously defined; J is boron or aluminum; and Q is a fluorinated C1-20 hydrocarbyl group. Most specifically, Q is independently selected from the group consisting of fluorinated aryl group, such as a pentafluorophenyl group (i.e., a $C_6F_5$ group) or a 3,5-bis$(CF_3)_2C_6H_3$ group. Illustrative, but not limiting, examples of boron compounds which may be used as an activating cocatalyst in the preparation of the improved catalysts of this invention are tri-substituted ammonium salts such as: trimethylammonium tetraphenylborate, triethylammonium tetraphenylborate, tripropylammonium tetraphenylborate, tri(n-butyl)ammonium tetraphenylborate, tri(tbutyl)ammonium tetraphenylborate, N,N-dimethylanilinium tetraphenylborate, N,N-diethylanilinium tetraphenylborate, N,N-dimethylanilinium tetra-(3,5-bis(trifluoromethyl)phenyl)borate, N,N-dimethyl-(2,4,6-trimethylanilinium) tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri (secbutyl)ammonium tetrakis(pentafluorophenyl)borate, N,Ndimethylanilinium tetrakis(pentafluorophenyl)borate, N,N-diethylanilinium tetrakis(pentafluorophenyl)borate, N,N-dimethyl-(2,4,6-trimethylanilinium)tetrakis(pentafluorophenyl)borate, trimethylammonium tetrakis-(2,3,4,6-tetrafluorophenylborate and N,N-dimethylanilinium tetrakis-(2,3,4,6-tetrafluorophenyl)borate; dialkyl ammonium salts such as: di-(i-propyl)ammonium tetrakis(pentafluorophenyl) borate, and dicyclohexylammonium tetrakis(pentafluorophenyl)borate; and tri-substituted phosphonium salts such as: triphenylphospnonium tetrakis(pentafluorophenyl)borate, tri (o-tolyl)phosphonium tetrakis(pentafluorophenyl)borate, and tri(2,6-dimethylphenyl)phosphonium tetrakis(pentafluorophenyl)borate; N,N-dimethylanilinium tetrakis(3,5-bis(trifluoromethyl)phenyl)borate; $HNMe(C_{18}H_{37})_2{}^+B(C_6F_5)_4{}^-$; $HNPh(C_{18}H_{37})_2{}^+B(C_6F_5)_4{}^-$ and $((4\text{-}nBu\text{-}Ph)NH(n\text{-}hexyl)_2)^+B(C_6F_5)_4{}^-$ and $((4\text{-}nBu\text{-}Ph)NH(n\text{-}decyl)_2)^+B(C_6F_5)_4{}^-$. Specific $(L^*\text{-}H)^+$ cations are N,N-dialkylanilinium cations, such as $HNMe_2Ph^+$, substituted N,N-dialkylanilinium cations, such as $(4\text{-}nBu\text{-}C_6H_4)NH(n\text{-}C_6H_{13})_2{}^+$ and $(4\text{-}nBu\text{-}C_6H_4)NH(n\text{-}C_{10}H_{21})_2{}^+$ and $HNMe(C_{18}H_{37})_2{}^+$. Specific examples of anions are tetrakis(3,5-bis(trifluoromethyl) phenyl)borate and tetrakis(pentafluorophenyl)borate. In some embodiments, the specific activator is $PhNMe_2H+B(C_6F_5)_4{}^-$.

Other suitable ion forming activators comprise a salt of a cationic oxidizing agent and a non-interfering, compatible anion represented by the formula:

$$(Ox^{e+})_d(A^{d-})_e$$

wherein: Oxe+ is a cationic oxidizing agent having a charge of e+; e is an integer from 1 to 3; and $A^{d-}$, and d are as previously defined. Examples of cationic oxidizing agents include: ferrocenium, hydrocarbyl-substituted ferrocenium, Ag+, or Pb+2. Specific embodiments of Ad– are those anions previously defined with respect to the Bronsted acid containing activating cocatalysts, especially tetrakis(pentafluorophenyl)borate.

Another suitable ion forming, activating cocatalyst comprises a compound that is a salt of a carbenium ion or silyl cation and a noninterfering, compatible anion represented by the formula:

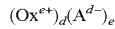

wherein:
 is a CI-100 carbenium ion or silyl cation; and $A^-$ is as previously defined. A preferred carbenium ion is the trityl cation, i.e. triphenylcarbenium. The silyl cation may be characterized by the formula $Z^4Z^5Z^6Si^+$ cation, where each of $Z^4$, $Z^5$, and $Z^6$ is independently selected from the group consisting of hydrogen, halogen, and optionally substituted alkyl, alkenyl, alkynyl, heteroalkyl, heteroalkenyl, heteroalkynyl, aryl, heteroaryl, alkoxyl, aryloxyl, silyl, boryl, phosphino, amino, mercapto, alkylthio, arylthio, and combinations thereof. In some embodiments, a specified activator is $Ph_3C^+ B(C_6F_5)_4{}^-$.

Other suitable activating cocatalysts comprise a compound that is a salt, which is represented by the formula $(A^{*+a})_b (Z^*J^*_j)^{-c}{}_d$ wherein A* is a cation of charge +a; Z* is an anion group of from 1 to 50, specifically 1 to 30 atoms, not counting hydrogen atoms, further containing two or more Lewis base sites; J* independently each occurrence is a Lewis acid coordinated to at least one Lewis base site of Z*, and optionally two or more such J* groups may be joined together in a moiety having multiple Lewis acidic functionality; j is a number form 2 to 12; and a, b, c, and d are integers from 1 to 3, with the proviso that a×b is equal to c×d. See, WO 99/42467, which is incorporated herein by reference. In other embodiments, the anion portion of these activating cocatalysts may be characterized by the formula $((C_6F_5)_3M''''\text{-}LN\text{-}M''''(C_6F_5)_3)^-$ where M'''' is boron or aluminum and LN is a linking group, which is specifically selected from the group consisting of cyanide, azide, dicyanamide and imidazolide. The cation portion is specifically a quaternary amine. See, e.g., LaPointe, et al., J. Am. Chem. Soc. 2000, 122, 9560-9561, which is incorporated herein by reference.

In addition, suitable activators include Lewis acids, such as those selected from the group consisting of tris(aryl)boranes, tris(substituted aryl)boranes, tris(aryl)alanes, tris(substituted aryl)alanes, including activators such as tris(pentafluorophenyl)borane. Other useful ion forming Lewis acids include those having two or more Lewis acidic sites, such as those described in WO 99/06413 or Piers, et al. "New Bifunctional Perfluoroaryl Boranes: Synthesis and Reactivity of the ortho-Phenylene-Bridged Diboranes 1,2-$(B(C_6F_5)_2)_2C_6X_4$ (X=H, F)", J. Am. Chem. Soc., 1999, 121, 3244-3245, both of which are incorporated herein by reference. Other useful Lewis acids will be evident to those of skill in the art. In general, the group of Lewis acid activators is within the group of ion forming activators (although exceptions to this general rule can be found) and the group tends to exclude the group 13 reagents listed below. Combinations of ion forming activators may be used.

Other general activators or compounds useful in a polymerization reaction may be used. These compounds may be activators in some contexts, but may also serve other functions in the polymerization system, such as alkylating a metal center or scavenging impurities. These compounds are within the general definition of "activator," but are not considered herein to be ion-forming activators. These compounds include a Group 13 reagent that may be characterized by the formula $G^{13}R^{50}{}_{3-p}D_p$ where $G^{13}$ is selected from the group consisting of B, Al, Ga, In and combinations thereof, p is 0, 1 or 2, each $R^{50}$ is independently selected from the group consisting of hydrogen, halogen, and optionally substituted alkyl, alkenyl, alkynyl, heteroalkyl, heteroalkenyl, heteroalkynyl, aryl, heteroaryl, and combinations thereof, and each D is independently selected from the group consisting of halogen, hydrogen, alkoxy, aryloxy, amino, mercapto, alkylthio, arylthio, phosphino and combinations thereof. In other embodiments, the Group 13 activator is an oligomeric or polymeric alumoxane compound, such as methylalumoxane and the known modifications thereof. See, for example, Barron, "Alkylalumoxanes, Synthesis, Structure and Reactivity", pp 33-67 in "Metallocene-Based Polyolefins: Preparation, Properties and Technology", Edited by J. Schiers and W. Kaminsky, Wiley Series in Polymer Science, John Wiley & Sons Ltd., Chichester, England, 2000, and references cited therein. In other embodiments, a divalent metal reagent may be used that is defined by the general formula M'R$^{50}_{2-p'}$D$_{p'}$, and p' is 0 or 1 in this embodiment and R$^{50}$ and D are as defined above. M' is the metal and is selected from the group consisting of Mg, Ca, Sr, Ba, Zn, Cd and combinations thereof. In still other embodiments, an alkali metal reagent may be used that is defined by the general formula M"R$^{50}$ and in this embodiment R$^{50}$ is as defined above. M" is the alkali metal and is selected from the group consisting of Li, Na, K, Rb, Cs and combinations thereof. Additionally, hydrogen and/or silanes may be used in the catalytic composition or added to the polymerization system. Silanes may be characterized by the formula SiR$^{50}_{4-q}$D$_q$ where R$^{50}$ is defined as above, q is 1, 2, 3 or 4 and D is as defined above, with the proviso that there is at least one D that is a hydrogen.

The activator or a combination of activators may be supported on an organic or inorganic support. Suitable supports include silicas, aluminas, clays, zeolites, magnesium chloride, polystyrenes, substituted polystyrenes. The activator may be co-supported with the metal-ligand complex. Suitable supports are more fully described in the section entitled "Catalyst Supports" above.

The molar ratio of metal:activator (whether a composition or complex is employed as a catalyst) employed specifically ranges from 1:10,000 to 100:1, more specifically from 1:5000 to 10:1, most specifically from 1:10 to 1:1. In one embodiment of the invention mixtures of the above compounds are used, particularly a combination of a Group 13 reagent and an ion-forming activator. The molar ratio of Group 13 reagent to ion-forming activator is specifically from 1:10,000 to 1000:1, more specifically from 1:5000 to 100:1, most specifically from 1:100 to 100:1. In another embodiment, the ion forming activators are combined with a Group 13 reagent. Another embodiment is a combination of the above compounds having about 1 equivalent of an optionally substituted N,N-dialkylanilinium tetrakis(pentafluorophenyl)borate, and 5-30 equivalents of a Group 13 reagent. In some embodiments from about 30 to 2000 equivalents of an oligomeric or polymeric alumoxane activator, such as a modified alumoxane (e.g., alkylalumoxane), can be used.

Slurry Phase Ethylene Polymerization

When combined with an activator as described above, the supported metal-ligand complex catalysts described herein are particularly well suited for use in the slurry phase polymerization of ethylene to produce very-high and ultra-high molecular weight polyethylene or a bimodal polymer composition comprising at least one VHMWPE or UHMWPE component.

To effect polymerization, the supported catalyst and the activator are initially slurried in a suitable solvent, generally a liquid hydrocarbon having from about 4 to about 14 carbon atoms, such as about 8 to about 12 carbon atoms. In addition, a compound effective to increase the conductivity of the hydrocarbon solvent is added to the slurry in an amount of about 5 to less than 40 ppm by volume, such as about 20 to about 30 ppm by volume, of the solvent. Generally, this anti-static agent comprises at least one of a polysulfone copolymer, a polymeric polyamine, and an oil-soluble sulfonic acid. A suitable anti-static agent is Octastat® 2000, 2500, 3000, 5000, or Statsafe® 2500, 3000, 5000, 6000 or 6633, or Atmer® 163. Further the slurry may contain a scavenger, such as an alkyl magnesium compound, typically in an amount between about 0.05 mmol and about 16 mmol, such as between about 0.5 mmol and about 16 mmol, per liter of the hydrocarbon solvent.

The resultant catalyst slurry is then contacted with ethylene under polymerization conditions which typically include a temperature about 20° C. to less than 90° C., such as about 50° C. to about 85° C., for example about 65° C. to about 85° C., and a pressure of about of about 4 bar to about 40 bar, such as about 4 bar to about 20 bar, for example about 4 bar to about 10 bar, for a time of about 15 minutes to about 600 minutes, for example about 15 minutes to about 300 minutes.

Control of the molecular weight of the polyethylene produced is effected by the addition of hydrogen typically in amounts between about 0% and about 10% of hydrogen by volume of the ethylene feed.

Polyethylene Product

The product of the slurry polymerization process described above is polyethylene powder having a molecular weight, as determined by ASTM 4020, of $3 \times 10^5$ g/mol, such as between about $3 \times 10^5$ g/mol and about $30 \times 10^6$ g/mol, or between about $1 \times 10^6$ g/mol and about $20 \times 10^6$ g/mol, or between about $3 \times 10^6$ g/mol and about $20 \times 10^6$ g/mol, or between about $3 \times 10^6$ g/mol and about $10 \times 10^6$ g/mol, or between about $3 \times 10^6$ g/mol and about $6 \times 10^6$ g/mol. The powder may have a monomodal molecular weight distribution or a bimodal molecular weight distribution, in the latter case with a first part of the powder having a molecular weight in the range of about $3 \times 10^6$ g/mol to about $30 \times 10^6$ g/mol and a second part powder having a molecular weight in the range of about $0.3 \times 10^6$ g/mol to about $10 \times 10^6$ g/mol. Generally, the amount of the second lower molecular weight fraction is in the range of 0 to 40%.

In addition, the present polyethylene powder typically has an average particle size, d50, between about 10 and about 1500 μm, generally between about 50 and about 1000 μm, often between about 60 and about 700 μm. In this respect, the polyethylene powder particle size measurements referred to herein are obtained by a laser diffraction method according to ISO 13320.

The bulk density of the present polyethylene powder is typically between about 0.13 and about 0.5 g/ml, generally between about 0.2 and about 0.5 g/ml, especially between about 0.25 and about 0.5 g/ml. Polyethylene powder bulk density measurements referred to herein are obtained by DIN 53466.

Further the polyethylene powder typically has a crystallinity of about 60 to about 85% and a molecular weight distribution (Mw/Mn) of about 2 to about 30.

Uses of the Polyethylene Product

The polyethylene powder produced by the present process can be used in all applications currently envisaged for conventional forms of VHMWPE and UHMWPE. Thus the powder can be compression molded or ram extruded into shaped articles for use in, for example, machine parts, linings, fenders, and orthopedic implants. Alternatively, the powder can be sintered in a mold at a temperature between about 140° C. and about 300° C. until the surfaces of individual polymer particles fuse at their contact points to form a porous structure.

The invention will now be more particularly described with reference to the following non-limiting Examples.

In the Examples UHMWPE was produced by slurry phase polymerization of ethylene in the presence of a catalyst comprising silica-supported ZrCl$_2$ bis(phenolate) ether complex and a triisobutylaluminium (TIBA) co-catalyst. The silica-supported complex was produced according to the following procedure.

Silica, which had previously been calcined at 600° C. for 5 hours under vacuum (500 mg), was placed in an 8 ml scintillation vial. The silica was slurried in toluene (3.5 mL) and PMAO-IP (Azko-Nobel) (2.333 mL of a 1.5 M solution in toluene) was added to the vortexing silica/toluene slurry. The reaction mixture was slurried for 30 minutes at room temperature and then heated to 50° C. The toluene was then removed by a stream of nitrogen with continuous vortexing and heating at 50° C. A dry material was obtained after 2.5 hours. The above preparation was repeated 3 times in different 8 mL vials. The material was further dried under vacuum at 50° C. for an additional hour resulting in 2.94 g of PMAO-IP/silica supported activator. The resulting supported catalyst had an Al loading of 4.98 mmol Al per gram PMAO-IP/Silica.

The PMAO-IP treated silica support was then slurried with a toluene solution of a $ZrCl_2$ bis(phenolate) ether complex having the formula:

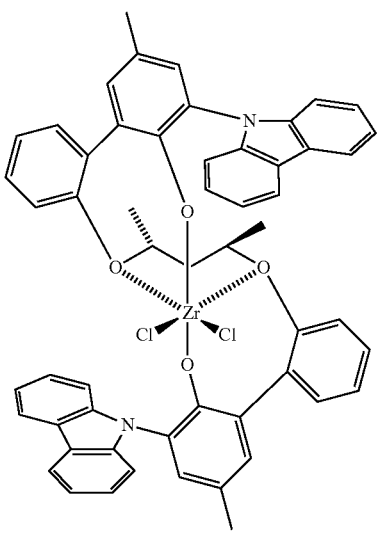

The bis(phenolate) ether ligand was synthesized as described in WO 2005/108406 and was complexed with $Zr(CH_2Ph)_2Cl_2(EtO)$ in toluene at 80-100° C. for 1-3 hours. The reaction mixture was concentrated and cooled to −30° C. over night. Pentane was added to the concentrated toluene reaction mixture before cooling. The complex was obtained as a crystalline material and was dissolved in toluene to give a solution with a concentration of 4.0 mM of the complex. The resultant solution (3.0 ml, 12.0 μmol) was added to a slurry of the PMAO-IP/Silica (4.98 mmol Al/g) (300 mg) in heptane (3.0 ml) in an 8 ml vial while vortexing. The slurry was shaken well and vortexed at room temperature for 2 hours and then dried by a small N2 stream with a needle through a septum at room temperature. This took about 1.5 hours. The yellow (slightly orange) material was further dried under vacuum. The resulting supported catalyst had an Al loading of 4.98 mmol Al per gram PMAO-IP/Silica and a transition metal loading of 40 μmol per gram final catalyst.

Example 1

Ethylene polymerization was conducted in a 3 liter reactor which was first flushed with argon and then conditioned with a mixture of a hydrocarbon solvent (a mixture of $C_8$ to $C_{12}$ aliphatic hydrocarbons) (1.5 liter) and an aluminium alkyl (TEA 200 mmol/l). After a conditioning time of 15 to 30 minutes, the liquids were evacuated. The reactor was then filled with 2 liter of the hydrocarbon solvent together with the appropriate amount of Octastat® 2000 to reach a concentration level of 30 ppm, and heated to 20° C. under stiffing (750 rpm). 2 mL of a 100 wt. % solution of triisobutylaluminium (TIBA; 8 mmol) were added into the reactor under nitrogen flow and the reactor was pressurized at seven bar ethylene pressure.

In the glove-box, 100 mg of the supported complex described above (corresponding to 40 μmol metal) were weighed into a dropping funnel and suspended in 30 mL of hydrocarbon solvent. The content of the dropping funnel was then transferred into a metal cartridge under argon flow, the cartridge was sealed and pressurised under nine bar argon. The catalyst suspension was injected into the reactor, whilst parameters like temperature, ethylene flow, ethylene pressure are monitored. After injection, the cartridge was rinsed with 40 mL hydrocarbon solvent. The reaction had to be terminated after 50 minutes.

Example 2

The same polymerization conditions as in Example 1 were used except that the polymerization temperature was 40° C. The reaction had to be terminated after 58 minutes.

Example 3

The same polymerization conditions as in Example 1 were used except that the polymerization temperature was 70° C. After 280 minutes reaction time, the ethylene feed is closed, the reactor cooled down to room temperature, vented, flushed with nitrogen for one hour and the polymer slurry is collected into a bucket. The polymer is then filtered, washed with isopropanol and dried at 80° C. overnight. A yield of 314 g free flowing powder was obtained equivalent to a catalyst activity of 3140 g/g (see Table 1).

Example 4

The same polymerization conditions as in Example 1 were used except that the polymerization temperature was 80° C. After 156 minutes reaction time, the ethylene feed is closed, the reactor cooled down to room temperature, vented, flushed with nitrogen for one hour and the polymer slurry is collected into a bucket. The polymer is then filtered, washed with isopropanol and dried at 80° C. overnight. A yield of 200 g free flowing powder was obtained equivalent to a catalyst activity of 4000 g/g (see Table 1).

Example 5

The same polymerization conditions as in Example 1 were used except that 9.2 mL of a 20 wt. % heptane solution of butyloctylmagnesium (BOM; 8 mmol) were added instead of TIBA. The temperature was 80° C. After 210 minutes reaction time, the ethylene feed is closed, the reactor cooled down to room temperature, vented, flushed with nitrogen for one hour and the polymer slurry is collected into a bucket. The polymer is then filtered, washed with isopropanol and dried at 80° C. overnight. A yield of 289 g free flowing powder was obtained equivalent to a catalyst activity of 5780 g/g (see Table 1).

Example 6

The same polymerization conditions as in Example 1 were used except that 9.2 mL of a 20 wt. % heptane solution of butyloctylmagnesium (BOM; 8 mmol) were added instead of TIBA. The temperature was 80° C. and the pressure nine bar. After 170 minutes reaction time, the ethylene feed is closed, the reactor cooled down to room temperature, vented, flushed with nitrogen for one hour and the polymer slurry is collected into a bucket. The polymer is then filtered, washed with isopropanol and dried at 80° C. overnight. A yield of 438 g free flowing powder was obtained equivalent to a catalyst activity of 8760 g/g (see Table 1).

TABLE 1

| Example | $P_{ethylene}$ (bar) | T (° C.) | Reaction time (min) | Productivity (g/g) |
|---|---|---|---|---|
| 1 | 7 | 20 | 50 | — |
| 2 | 7 | 40 | 58 | — |
| 3 | 7 | 70 | 280 | 3140 |
| 4 | 7 | 80 | 156 | 4000 |
| 5 | 7 | 80 | 210 | 5780 |
| 6 | 9 | 80 | 170 | 8760 |

The invention claimed is:

1. A process for producing high molecular weight polyethylene having a molecular weight of at least $3 \times 10^5$ g/mol as determined by ASTM D 4020, the process comprising: contacting ethylene under polymerization conditions with a slurry of a catalyst composition comprising a Group 4 metal complex of a phenolate ether ligand, wherein the polymerization conditions comprise a temperature of 50° C. to 85° C. and a pressure of 4 bar to 40 bar.

2. The process of claim 1 wherein the polymerization conditions comprise a pressure of 4 bar to 20 bar.

3. The process of claim 1 wherein the Group 4 metal complex is a complex of a bis(phenolate) ether ligand.

4. The process of claim 1 wherein the Group 4 metal complex has the following general formula:

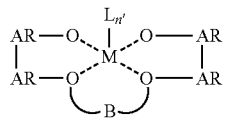

wherein at least two of the bonds from the oxygens (O) to M are covalent, with the other bonds being dative; AR is an aromatic group that can be the same or different from the other AR groups with each AR being independently selected from the group consisting of optionally substituted aryl and optionally substituted heteroaryl; B is a bridging group having from 3 to 50 atoms not counting hydrogen atoms and is selected from the group consisting of optionally substituted divalent hydrocarbyl and optionally substituted divalent heteroatom-containing hydrocarbyl; M is a metal selected from the group consisting of Hf and Zr; each L is independently a moiety that forms a covalent, dative or ionic bond with M; and n' is 1, 2, 3 or 4.

5. The process of claim 1 wherein the phenolate ether ligand has the following general formula:

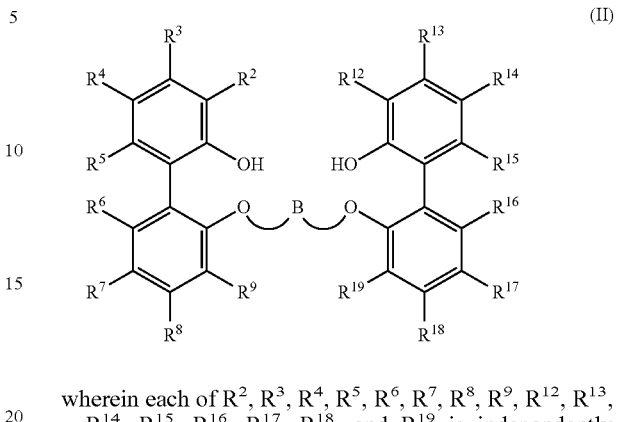

wherein each of $R^2$, $R^3$, $R^4$, $R^5$, $R^6$, $R^7$, $R^8$, $R^9$, $R^{12}$, $R^{13}$, $R^{14}$, $R^{15}$, $R^{16}$, $R^{17}$, $R^{18}$, and $R^{19}$ is independently selected from the group consisting of hydrogen, halogen, and optionally substituted hydrocarbyl, heteroatom-containing hydrocarbyl, alkoxy, aryloxy, silyl, boryl, phosphino, amino, alkylthio, arylthio, nitro, and combinations thereof; optionally two or more R groups can combine together into ring structures having from 3 to 12 atoms in the ring (not counting hydrogen atoms); and B is a bridging group having from 3 to 50 atoms not counting hydrogen atoms and is selected from the group consisting of optionally substituted divalent hydrocarbyl and optionally substituted divalent heteroatom-containing hydrocarbyl.

6. The process of claim 5, wherein two or more R groups combine together into a single ring structure.

7. The process of claim 5, wherein two or more R groups combine together into multiple ring structures.

8. The process of claim 1 wherein the phenolate ether ligand is selected from:

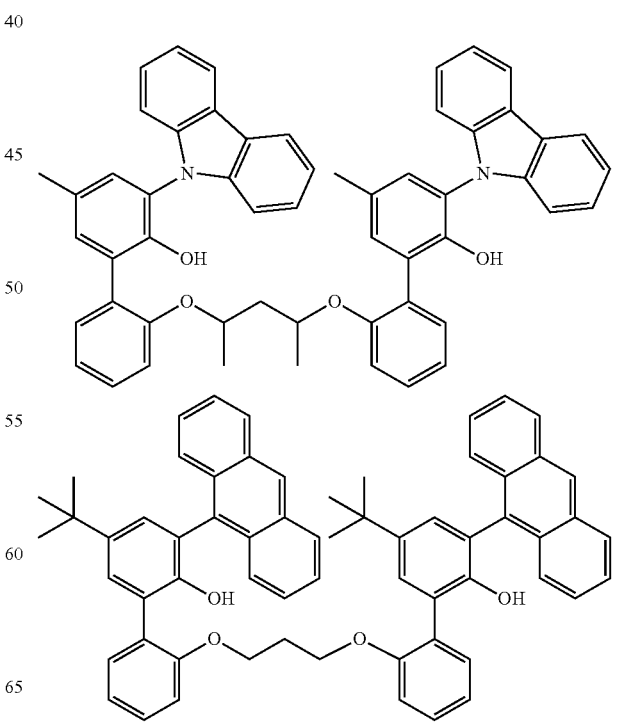

-continued

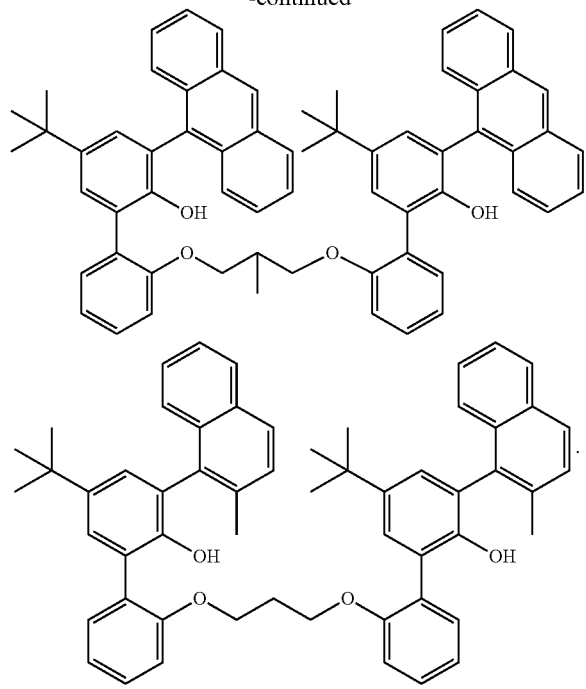

9. The process of claim 1 wherein the Group 4 metal is zirconium.

10. The process of claim 1 wherein the Group 4 metal complex is disposed on a particulate support.

11. The process of claim 10 wherein the particulate support has an average particle size, $d_{50}$, of less than 58 microns.

12. The process of claim 10 wherein the particulate support has an average particle size, $d_{50}$, of less than 50 microns.

13. The process of claim 10 wherein the particulate support has an average particle size, $d_{50}$, of less than 30 microns.

14. The process of claim 10 wherein the particulate support has an average particle size, $d_{50}$, of from 4 to 20 microns.

15. The process of claim 10 wherein the particulate support has a span, $\log_{in}(d_{90}/d_{10})$ less than 0.6.

16. The process of claim 10 wherein the particulate support comprises an inorganic oxide.

17. The process of claim 16 wherein the particulate support comprises silica.

18. The process of claim 10 wherein the particles of the support are substantially spherical.

19. The process of claim 10 wherein the particles of the support are treated with an organoaluminum compound before said Group 4 metal complex is deposited on the support.

20. A compound having one of the following formulae:

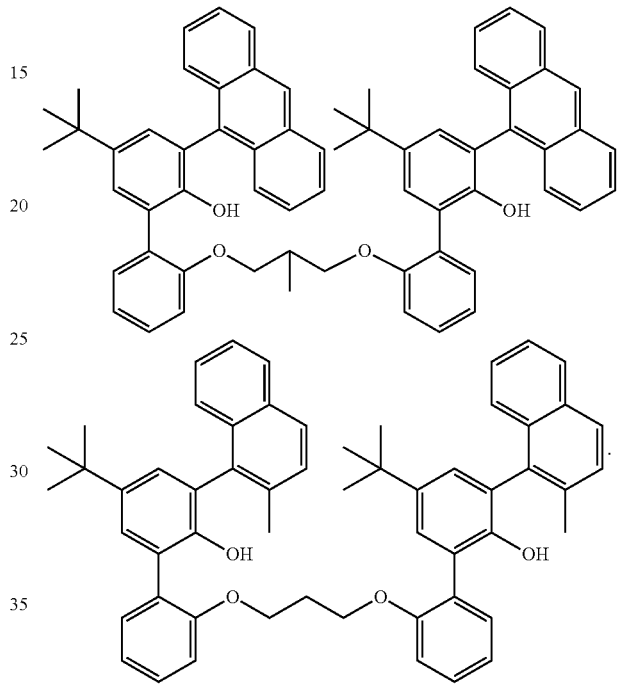

21. A complex of a Group 4 metal compound selected from zirconium or hafnium, and a ligand comprising the compound of claim 20.

* * * * *